US007189513B2

(12) United States Patent
Khleif et al.

(10) Patent No.: US 7,189,513 B2
(45) Date of Patent: Mar. 13, 2007

(54) HUMAN PAPILLOMA VIRUS IMMUNOREACTIVE PEPTIDES

(75) Inventors: Samir N. Khleif, Silver Spring, MD (US); Jay A. Berzofsky, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 213 days.

(21) Appl. No.: 10/472,661

(22) PCT Filed: Mar. 22, 2002

(86) PCT No.: PCT/US02/09261

§ 371 (c)(1),
(2), (4) Date: Sep. 22, 2003

(87) PCT Pub. No.: WO02/077012

PCT Pub. Date: Oct. 3, 2002

(65) Prior Publication Data

US 2004/0106551 A1 Jun. 3, 2004

Related U.S. Application Data

(60) Provisional application No. 60/278,520, filed on Mar. 23, 2001.

(51) Int. Cl.
*C12Q 1/68* (2006.01)
(52) U.S. Cl. .......................... 435/6; 435/69.1; 435/325
(58) Field of Classification Search .................... 435/6, 435/235.1, 325, 69.1
See application file for complete search history.

(56) References Cited

U.S. PATENT DOCUMENTS

| | | | |
|---|---|---|---|
| 4,551,270 A | 11/1985 | Danos et al. | 530/327 |
| 4,777,239 A | 10/1988 | Schoolnik et al. | 530/326 |
| 5,279,833 A | 1/1994 | Rose | 424/450 |
| 5,580,859 A | 12/1996 | Felgner et al. | 514/44 |
| 5,589,466 A | 12/1996 | Felgner et al. | 514/44 |
| 5,719,054 A | 2/1998 | Boursnell et al. | 435/320 |
| 5,985,270 A * | 11/1999 | Srivastava | 424/93.71 |
| 6,004,557 A | 12/1999 | Edwards et al. | 424/192.1 |
| 6,183,746 B1 | 2/2001 | Urban et al. | 424/186.1 |

FOREIGN PATENT DOCUMENTS

| | | |
|---|---|---|
| AU | 75535/87 | 1/1988 |
| EP | 256321 | 1/1988 |
| EP | 386734 | 9/1990 |
| EP | 412762 | 2/1991 |
| FR | 2643817 | 9/1990 |
| JP | 01061665 | 3/1989 |
| WO | WO 86/05816 | 10/1986 |
| WO | WO 87/01375 | 3/1987 |
| WO | WO 90/10867 | 10/1990 |
| WO | WO 91/06309 | 5/1991 |
| WO | WO 93/22338 | 11/1993 |
| WO | WO 93/24640 | 12/1993 |
| WO | WO 94/03205 | 2/1994 |
| WO | WO 94/20127 | 9/1994 |
| WO | WO 96/40095 | 12/1996 |
| WO | WO 97/41440 | 11/1997 |

OTHER PUBLICATIONS

Abcarian et al., "The Immunotherapy of Anal Condyloma Acuminatum." *Dis. Colon Rectum.* 19(3):237-244 (Apr. 1976).
Abcarian et al., "Long-term Effectiveness of the Immunotherapy of Anal Condyloma Acuminatum." *Dis. Colon Rectum.* 25(7):648-651 (Oct. 1982).
Abcarian et al., "The Effectiveness of Immnotherapy in the Treatment of Anal Condyloma Acuminatum. " *J. Surg. Res.* 22:321-236 (1977).
Babbitt et al., "Binding of immunogenic peptides to Ia histocompatibility molecules." *Nature* 317:359-361 (Sep. 1985).
Brown et al., "Three-dimensional structure of the human class II histocompatibility antigen HLA-DR1." *Nature* 364:33-39 (Jul. 1, 1993).
Bunney, "Viral warts: a new look at an old problem." *Br. Med. J.* 293:1045-1047 (Oct. 25, 1986).
Buus et al., "Isolation and Characterization of Antigen-Ia Complexes Involved in T Cell Recognition." *Cell* 47:1071 (1986).
Engelhard, "Structure of peptides associated with MHC class I molecules." *Curr. Opin. Immunol.* 6:13-23 (1994).
Felgner et al., "Lipofection: A highly efficient, lipid-mediated DNA-transfection procedure." *Proc. Natl. Acad. Sci. USA* 84:7413-7417 (Nov. 1987).
Frazer et al., "Association between anorectal dysplasia, human papillomavirus, and human immunodeficiency virus infection in homosexual men." *Lancet* 657-660 (Sep. 20, 1986).
Fremont et al., "Crystal Structure of I-A$^k$ in Complex with a Dominant Epitope of Lysozyme." *Immunity* 8:305-317 (Mar. 1998).
Fremont et al., "Crystal Structures of Two Viral Peptides in Complex with Murine MHC Class I H-2K$^b$," *Science* 257:919-927 (Aug. 14, 1992).
Germain and Margulies, "The biochemistry and cell biology of antigen processing and presentation." *Annu. Rev. Immunol.* 11:403-450 (1993).
Guo et al., "Different length peptides bind to HLA-Aw68 similarly at their ends but bulge out in the middle." *Nature* 360:364-366 (Nov. 26, 1992).
Guo et al., "Comparison of the P2 specificity pocket in three human histocompatibility antigens: HLA-A*6801, HLA-A*0201, and HLA-B*2705." *Proc. Natl. Acad. Sci. USA* 90:8053-8057 (Sep. 1993).

(Continued)

*Primary Examiner*—Ali R. Salimi
(74) *Attorney, Agent, or Firm*—Needle & Rosenberg, P.C.

(57) ABSTRACT

This invention provides immunogenic peptides from the HPV-18E6 protein that comprise class I restricted T cell epitopes and discloses methods of administering these peptides to individuals, and a method for monitoring or evaluating an immune response to HPV with these peptides.

6 Claims, 2 Drawing Sheets

OTHER PUBLICATIONS

Jamieson et al., "Effective Clearance of a Persistent Viral Infection Requires Cooperation between Virus-Specific Lyt2+ T Cells and Nonspecific Bone Marrow-Derived Cells." *J. Virol.* 61(12):3930-3937 (Dec. 1987).

Jones, "MHC class I and class II structures." *Curr. Opin. Immunol.* 9:75-79 (1997).

Kast et al., "Role of HLA-A Motifs in Identification of Potential CTL Epitopes in Human Papillomavirus Type 16 E6 and E7 Proteins." *J. Immunol.* 152:3904-3912 (1994).

Kirschner, "Immunobiology of Human Papillomarirus Infection." *Prog. Med. Virol.* 33:1-41 (1986).

Kondo et al., "Prominent Roles of Secondary Anchor Residues in Peptide Binding to HLA-A24 Human Class I Molecules." *J. Immunol.* 155:4307-4312 (1995).

Lukacher et al. *J Exp Med.* 160:814-826 (1994).

Madden et al., "The Three-Dimensional Structure of HLA-B27 at 2.1 Å Resolution Suggests a General Mechanism for Tight Peptide Binding to MHC." *Cell* 70:1035-1048 (Sep. 18, 1992).

Madden et al., "The Antigenic Identity of Peptide-MHC Complexes: A Comparison of the Conformations of Five Viral Peptides Presented by HLA-A2." *Cell* 75:693-708 (Nov. 19, 1993).

Madden. "The three-dimensional structure of peptide-MHC complexes." *Annu. Rev. Immunol.* 13:587-622 (1995).

Mannino and Gould-Fogerite. "Liposome Mediated Gene Transfer." *Bio Techniques.* 6(7):682-690 (1988).

Matsumura et al., "Emerging Principles for the Recognition of Peptide Antigens by MHC Class I Molecules." *Science* 257:927-934 (Aug. 14, 1992).

McMichael et al., "Cytotoxic T-cell immunity influenza." *N. Eng. J. Med.* 309(1):13-17 (Jul. 7, 1983).

Meneguzzi et al., "Vaccinia recombinants expressing early bovine papilloma virus (BPV1) proteins: retardation of BPV1 tumour development." Vaccine 8:199-204 (Jun. 1990).

Oldstone et al., "Cytoimmunotherapy for persistent virus infection reveals a unique clearance pattern from the central nervous system." *Nature* 321:239-243 (May 15, 1989).

Olson et al., "Induced Immunity of Skin, Vagina, and Urinary Bladder to Bovine Papillomatosis." *Cancer Res.* 22:463-469 (May 1962).

Olson et al., "Immuntiy to Bovine Cutaneous Papillomatosis Produced by Vaccine Homologous to the Challenge Agent." *J. Am. Vet. Med. Assoc.* 135(10):499-502 (Nov. 15, 1959).

Parham et al., "The Origins of HLA-A,B,C Polymorphism." *Immunol. Rev.* 143:141-180 (1995).

Pilacinski et al., "Development of a recombinant DNA vaccine against bovine papillomavirus infection in cattle." *UCLA Symp Molecular and Cellular Biology New Series.* vol. 32. *Papilloma Viruses Molecular and Clinical Aspects.* Alan R. Liss, New York. p. 257-271 (1985).

Quinnan et al., "Cytotoxic T-cells in Cytomegalovirus Infection: HLA_Restricted T-Lymphocyte and Non-T-Lymphocyte Cytotoxic Responses Correlate with Recovery from Cytomegalovirus Infection in Bone-Marrow-Transplant Recipients." *N. Eng. J. Med.* 307(1):7-13 (Jul. 1, 1982).

Rammensee et al., "MHC ligands and peptide motifs: first listing." *Immunogenetics* 41:178-228 (1995).

Reddenhase et al., "Intestitial Murine Cytomegalovirus Pneumonia After Irradiation: Characterization of Cells That limit Viral Replication During Established infection of the Lungs." *J. Virol.* 55(2):263-273 (Aug. 1985).

Ruppert et al., "Prominent Role of Secondary Anchor Residues in Peptide Binding to HLA-A2.1 Molecules." *Cell* 74:929-937 (Sep. 10, 1993).

Saper et al., "Refined Structure of the Human Histocompatibility Antigen HLA-A2 at 2-6 Å Resolution." *J. Mol. Biol.* 219:277-319 (1991).

Sethi et al., "Protection of Mice from Fatal Herpes Simplex Virus Type 1 Infection by Adoptive Transfer iof Cloned Virus-specific and H-2-restricted Cytotoxic T Lymphocytes." *J. Gen. Virol.* 64:443-447 (1983).

Sette and Grey. "Chemistry of peptide interactions with MHC proteins." *Curr. Opin. Immunol.* 4:79-86 (1992).

Sette et al., "HLA supertypes and supermotifs: a fuctional perspective on HLA polymorphism."*J. Curr. Opin. Immunol.* 10:478-482 (1998).

Sheil et al. *Ninth Report of Australian and New Zealand Combined Dialysis and Transplant Registry.* APS Disney, ed. 104-112 (1986).

Sidney et al., "Definition of an HLA-A3_Like Supermotif Demonstrates the Overlapping Peptide-Binding Repertiores of Common HLA Molecules." *Hum. Immunol.* 45:79-93 (1996).

Sidney et al., "Specificity and Degeneracy in Peptide Binding to HLA-B7-Like Class I Molecules." *J. Immunol.* 157:3480-3490 (1996).

Silver et al., "Atomic structure of a human MHC molecule presenting an influenza virus peptide." *Nature* 360:367-369 (Nov. 26, 1992).

Singer et al., "Genital wart virus infections: nuisance of potentially lethal?" *Br. Med. J.* 288:735-736 (Mar. 10, 1984).

Sommer and Sternberg. "Apoptosis and change of competence limit the size of the vulva equivalence group in *Pristionchus pacificus*: a genetic analysis." *Curr. Biol.* 6(1):52-59 (1994).

Smith et al., "An Altered Position of the α2 Helix of MHC Class I Is Revealed by the Crystal Structure of HLA-B-3501." *Immunity* 4:203-213 (Mar. 1996).

Southwood et al., "Serveral Common HLA-DR Types Share Largely Overlapping Peptide Binding Repertoires[1,2]." *J. Immunol.* 160:3363-3373 (1998).

Stern and Wiley; "Antigenic peptide binding by class I and class II histocompatiblility proteins." *Structure* 2(4):245-251 (Apr. 15, 1994).

Tigges et al., "Human CD8+ Herpes Simplex Virus-Specific Cytotoxic T-Lymphocyte Cones Recognize Diverse Virion Protein Antigens." *J Virol.* 66(3):1622-1634 (Mar. 1993).

Townsend et al., "Antigen recognition by class I-restricted T lymphocytes." *Annu. Rev. Immunol.* 7:601-624 (1989).

Watari et al., "A synthetic peptide induces long-term protection from lethal infection with herpes simplex virus 2." *J. Exp. Med.* 165:459-470 (1987).

Yap et al., "Transfer of specific cytotoxic T lymphocytes protects mice inoculated with influenza virus." *Nature* 273:238-239 (May 18, 1978).

Yasukawa et al., "Differential in vitro activation of cd4+cd8− and cd8+cd4− herpes simplex virus-specific human cytotoxic T clells." *J. Immunol.* 143(6):2051-2057 (Sep. 15, 1989).

Castellanos et al., "Synthetic Peptides Induce a Cytotoxic Response Against Human Papillomavirus Type-18", Gynecologic Oncology, vol. 82, No. 1, Jul. 2001.

Rudolf et al., "Human T-cell Responses to HLA-A-Restricted High Binding Affinity Peptides of Human Papillomavirus Type 18 Proteins E6 and E7", Clinical Cancer Research, vol. 7, No. 3, Mar. 2001.

Ressing et al., "Human CTL Epitopes Encoded by Human Papillomavirus Type 16 E6 and E7 Identified Through In Vivo and In Vitro Immunogenicity Studies of HLA-A-0201-Binding Peptides", Journal of Immunology, vol. 154, pp. 5934-5943, 1995.

Yoon et al., "Synthetic Peptides of Human Papillomavirus Type 18 E6 Harboring HLA-A2.1 Motif Can Induce Peptide-Specific Cytotoxic T-Cells from Peripheral Blood Mononuclear Cells of Health Donors", Virus Research, vol. 54, No. 1, Mar. 1998.

\* cited by examiner

SEQUENCE LISTING

```
<160> NUMBER OF SEQ ID NOS: 9

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 1

Lys Leu Pro Asp Leu Cys Thr Glu Leu
1               5
```

```
<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 2

Asp Arg Ala His Tyr Asn Ile
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 3

Ile Val Cys Pro Ile Cys Ser Gln
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 4

Leu Leu Met Gly Thr Leu Gly Ile Val
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 5

Thr Leu Gly Ile Val Cys Pro Ile Cys
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 6

Thr Leu Gly Ile Val Cys Pro Ile Cys
1               5

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 7
```

```
Leu Leu Met Gly Thr Leu Gly Ile Val Cys Pro
 1               5                   10

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 8

Thr Leu Gly Ile Val Cys Pro Ile
 1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 9

Gly Thr Leu Gly Ile Val Cys Pro Ile
 1               5
```

HUMAN PAPILLOMA VIRUS IMMUNOREACTIVE PEPTIDES

CROSS-REFERENCES TO RELATED APPLICATIONS

This application claims priority to U.S. provisional patent application Ser. No. 60/278,520, filed Mar. 23, 2001. The 60/278,520 provisional patent application is herein incorporated by its reference in its entirety.

STATEMENT AS TO RIGHTS TO INVENTIONS MADE UNDERFEDERALLY SPONSORED RESEARCH AND DEVELOPMENT

This invention is owned by the United States Government.

FIELD OF THE INVENTION

This invention relates to treatment of human papilloma virus (HPV) infection and in particular it relates to immunogenic peptides which are suitable for use in vaccines. This invention also relates to methods of using immunogenic peptides suitable for stimulating in vitro, lymphocytes or antigen presenting cells previously isolated from a patient and returning these stimulated cells to the patient. This invention relates to methods of monitoring the immune response in a patient exposed to these immunogenic peptides.

BACKGROUND OF THE INVENTION

Papilloma viruses are non-enveloped DNA viruses with a double stranded circular genome of approximately 8,000 bp. Over 75 types of human papilloma viruses (HPV) have been typed at the DNA level, and these can be broadly grouped into families on the basis of their tissue tropism.

Histologic, molecular, and epidemiologic evidence have implicated some HPV strains in cervical dysplasia and cervical cancer. Many studies support the view that most moderate and severe cervical intraepithelial neoplasias (CIN) contain HPV DNA which is exclusively detected in the histologically abnormal epithelium of these lesions. Persistent infection with HPV is believed to be the predominant risk factor for development of cervical carcinoma. HPV DNA is readily found in episomal form within cells exhibiting a cytopathic effect, while the HPV DNA is found integrated within the chromosomes of cells associated with most high grade pre-cancerous lesions and cancer. Approximately 23 HPV types are commonly found in anogenital screening programs, but only 10–15 are associated with progressive disease. Type 16 is the type most commonly found in cervical cancer tissue.

Papillomaviruses contain nine open reading frames. HPV genes with transforming properties have been mapped to open reading frames E6 and E7. Substantial biochemical work has demonstrated that the HPV E6 protein inactivates the protein p53, whereas the E7 protein interferes with retinoblastoma (Rb) protein function. Since p53 and Rb are tumor-suppressor proteins which function as cell division inhibitors, their inactivation by E6 and E7 leads the cell to enter into S phase of the cell cycle. Expression of E6 and E7 is sufficient to immortalize some primary cell lines, and blocking E6 or E7 function has been shown to reverse the transformed state.

Abundant circumstantial evidence implicates host immune mechanisms in the control of HPV associated tumours of the anogenital epithelium (Singer et al., *British Medical Journal* 288: 735–736, 1984). There is an increased incidence of pre-neoplastic (Frazer et al., *Lancet* ii 657–660, 1986) and neoplastic associated lesions in homosexual men immunosuppressed by human immunodeficiency virus infection and a markedly increased risk of squamous cell carcinoma (SCC) of the cervix and vulva but not of control organs such as breast and rectum in immunosuppressed allograft recipients (Sheil and Plavel *Ninth Report of Australian and New Zealand Combined Dialysis and Transplant Registry* pp 104–112 Edited by APS Disney 1986).

Taken with the above, the normal natural history of HPV infection in most patients with alpha-gamma globulinemia suggests that cellular rather than humoral responses are important for the control of the phenotypic expression of HPV infection (Kirschner *Progress in Medical Virology*, 1986).

Standard immunological approaches to the study of anogenital HPV infection have been hampered by the lack of a suitable animal model and of an in vitro epithelial cell culture permissive for HPV. Vaccines have also been proposed in regard to HPV with however only indifferent success.

It has been proposed to use vaccines containing autogenous tumor homogenates (Abcarian et al., *J. Surg Res* 22: 231–236, 1977, *Dis. Colon Rectum* 25:648–51, 1982, *Dis. Colon Rectunt* 19: 237–244, 1976. However it has recently been advocated that patients should no longer be treated with autogenous vaccines because of the potential oncogenic effect of the viral DNA (Bunney *Br Med. J* 293:1045–1047, 1986).

Data on successful prophylactic vaccination exist only for bovine fibropapillomas homogenized homogenate of bovine fibropapillomas and has been shown to provide limited immunity (Olson et al., *J Am Vet Med. Assoc.* 135: 499, 1959, *Cancer Res* 22: 463, 1962). A vaccine including an engineered L1 fusion protein (Pilacinski et al., *UCLA Symp. Molecular and Cellular Biology New Series* Vol 32 *Papilloma Viruses Molecular and Clinical Aspects* Alan R Liss New York, pg. 257,1985) has also been used in calves but proved unsuccessful in humans. In Pfister, PAPILLOMA VIRUSES AND HUMAN CANCER, CRC Press Inc. (1990) it is stated that there is presently no evidence for a possible prevention of HPV infection by the use of a capsid protein vaccine, but induction of an anti-tumor cell immunity appears to be feasible.

The L1 and L2 genes have been the basis of vaccines for the prevention and treatment of papilloma virus infections and immunogens used in the diagnosis and detection of papilloma viruses (International Patent Specifications WO 86/05816 and E 08303623). However, it appears that no commercial usage of these vaccines have taken place.

Reference may also be made to Patent Specification EP 386734 which describes new immunogenic regions of HPV-16 E7 protein which may be useful in vaccines, EP 375555 which describes HPV-16 peptides useful as immunoassay reagents for the detection of HPV-16 proteins and which contain an antigenic determinant for HPV16, a reference in VACCINE 83: 199–204 (1990) which describes vaccines including recombinants expressing HPV E5, E6 or E7 ORF intended for use in providing antitumor activity, Australian Specification 52860/90 which describes screening antibodies for specificity to an antigen which is an epitope of HPV-16 L1 or E7 proteins, Australian Specification 75535/87 which describes synthetic peptides of HPV corresponding to an amino acid sequence region having at least one reverse turn and predicted hydrophilicity, Patent Specification EP 217919 which describes type specific papillomavirus DNA sequences and peptides useful in vaccines containing 15–75 nucleotides, U.S. Pat. No. 4,551,270 which describes at least one antigenic determinant of papillomavirus and immunogens and vaccines containing the antigenic determinant, Patent Specification EP 412762 which describes a polypeptide, which inhibits binding of the HPV E7 protein to retinoblastoma gene which may be used in vaccines for treatment of cervical cancer and genital warts, French Specification 2643817 which describes a vaccine for treatment of tumours induced by papillomavirus containing recombinant poxvirus with heterologous DNA encoding region of non structural papillomavirus, Japanese Specification J01061665 which describes antibodies formed to an antigen polypeptide of HPV-16E6 or E7 protein, Australian Specification 76018/87 which describes expression products of HPV-16 or HPV-18 which may be used for the production of antibodies, EP235187 which describes kits containing polypeptide(s) expressed by several groups of papilloma virus including HPV-16 and HPV-18 which are expression products of E6, E7 or L2 genes and U.S. Pat. No. 4,777,239 which includes, diagnostic synthetic peptides for HPV one of which includes residues 45–58 of protein E6 and 40–50 of protein E7 which may be used as a therapeutic agent.

Virus-specific, human leukocyte antigen (HLA) class I-restricted cytotoxic T lymphocytes (CTL) are known to play a major role in the prevention and clearance of virus infections in vivo (Oldstone et al, *Nature* 321:239, 1989; Jamieson et al., *J. Virol.* 61:3930, 1987; Yap et al, *Nature* 273:238, 1978; Lukacher et al., *J. Exp. Med.* 160:814, 1994; McMichael et al., *N. Engl. J. Med.* 309:13, 1983; Sethi et al., *J. Gen. Virol.* 64:443, 1983; Watari et al., *J. Exp. Med.* 165:459, 1987; Yasukawa et al, *J. Immunol.* 143:2051, 1989; Tigges et al., *J. Virol.* 66:1622, 1993; Reddenhase et al. *J. Virol.* 55:263, 1985; Quinnan et al., *N. Engl. J. Med.* 307:6, 1982). HLA class I molecules are expressed on the surface of almost all nucleated cells. Following intracellular processing of antigens, epitopes from the antigens are presented as a complex with the HLA class I molecules on the surface of such cells. CTL recognize the peptide-HLA class I complex, which then results in the destruction of the cell bearing the HLA-peptide complex directly by the CTL and/or via the activation of non-destructive mechanisms e.g., the production of interferon, that inhibit viral replication.

SUMMARY OF THE INVENTION

This invention applies our knowledge of the mechanisms by which antigen is recognized by T cells, for example, to develop epitope-based vaccines directed towards HPV. More specifically, this application communicates our discovery of specific epitope pharmaceutical compositions and methods of use in the prevention and treatment of HPV infection.

Upon development of appropriate technology, the use of epitope-based vaccines has several advantages over current vaccines, particularly when compared to the use of whole antigens in vaccine compositions. There is evidence that the immune response to whole antigens is directed largely toward variable regions of the antigen, allowing for immune escape due to mutations. The epitopes for inclusion in an epitope-based vaccine are selected from conserved regions of viral or tumor-associated antigens, which thereby reduces the likelihood of escape mutants. Furthermore, immunosuppressive epitopes that may be present in whole antigens can be avoided with the use of epitope-based vaccines.

An additional advantage of an epitope-based vaccine approach is the ability to combine selected epitopes (CTL and HTL), and further, to modify the composition of the epitopes, achieving, for example, enhanced immunogenicity. Accordingly, the immune response can be modulated, as appropriate, for the target disease. Similar engineering of the response is not possible with traditional approaches.

Another major benefit of epitope-based immune-stimulating vaccines is their safety. The possible pathological side effects caused by infectious agents or whole protein antigens, which might have their own intrinsic biological activity, is eliminated.

An epitope-based vaccine also provides the ability to direct and focus an immune response to multiple selected antigens from the same pathogen. Thus, patient-by-patient variability in the immune response to a particular pathogen may be alleviated by inclusion of epitopes from multiple antigens from that pathogen in a vaccine composition. A "pathogen" may be an infectious agent or a tumor associated molecule.

One of the most formidable obstacles to the development of broadly efficacious epitope-based immunotherapeutics, however, has been the extreme polymorphism of HLA molecules. To date, effective non-genetically biased coverage of a population has been a task of considerable complexity; such coverage has required that epitopes be used that are specific for HLA molecules corresponding to each individual HLA allele, therefore, impractically large numbers of epitopes would have to be used in order to cover ethnically diverse populations. Thus, there has existed a need for peptide epitopes that are bound by multiple HLA antigen molecules for use in epitope-based vaccines. The greater the number of HLA antigen molecules bound, the greater the breadth of population coverage by the vaccine.

In a preferred embodiment, epitopes for inclusion in vaccine compositions and the methods of the invention are found in Table 1.

Furthermore, as described herein in greater detail, a need has existed to modulate peptide binding properties, for example, so that peptides that are able to bind to multiple HLA antigens do so with an affinity that will stimulate an immune response. Identification of epitopes restricted by more than one HLA allele at an affinity that correlates with immunogenicity is important to provide thorough population coverage, and to allow the elicitation of responses of sufficient vigor to prevent or clear an infection in a diverse segment of the population. Such a response can also target a broad array of epitopes.

The invention also includes an embodiment comprising a method for monitoring or evaluating an immune response to HPV in a patient having a known HLA-type, the method comprising incubating a T lymphocyte sample from the patient with a peptide composition comprising an HPV epitope consisting essentially of an amino acid sequence described in Table 1 which binds the product of at least one HLA allele present in said patient, and detecting the presence of a T lymphocyte that binds to the peptide.

A method of inducing a cytotoxic T lymphocyte response against human papilloma virus 16 (HPV 16) in a patient is provided, the method comprising contacting cytotoxic T cells from a patient with an immunogenic peptide of 20 amino acid residues or less comprising a cross-reactive peptide from the E6 protein of a related HPV strain, HPV 18, that has higher affinity for the HLA-A2.1 molecule than the corresponding epitope from HPV 16 itself, said peptide comprising the sequence X₁KLPDLCTEL(SEQ ID NO:1) X₂, wherein X₁ and X₂ are peptides of 0–11 amino acids in length comprising either native or non-native amino acid sequence and returning said cytotoxic T cells to the patient in an amount sufficient to induce a cytotoxic T cell response. X₁ or X₂ can comprise an HLA binding motif other than HLA-A2. X₁ or X₂ can comprise an amino acid sequence capable of binding to an HLA class II molecule. The peptide can be bound to an HLA molecule on an antigen presenting cell or the peptide can be bound to an HLA molecule on a lymphocyte. The HLA molecule can be HLA-A2, or the HLA molecule can be an HLA molecule other than HLA-A2.

A method for inducing an immune response against human papilloma virus 16 (HPV 16) is provided, comprising administering to a subject a composition, which is selected from a group consisting of:
 (i) a peptide of 20 amino acids or less comprising a cross-reactive peptide from the E6 protein of a related HPV strain, HPV 18, that has higher affinity for the HLA-A2.1 molecule than the corresponding epitope from HPV 16 itself, said peptide comprising the sequence X₁KLPDLCTEL(SEQ ID NO:1)X₂, wherein X₁ and X₂ are peptides of 0–11 amino acids in length comprising either native or non-native amino acid sequences; (ii) an antigen presenting cell pulsed with said peptide; and (iii) a cell sensitized in vitro to said peptide. The composition can be in a pharmaceutically acceptable carrier or in a sterile medium. The method can further comprise co-administering to the subject an immune adjuvant selected from non-specific immune adjuvants, subcellular microbial products and fractions, haptens, immunogenic proteins, immunomodulators, interferons, thymic hormones and colony stimulating factors. The administration step can comprise sensitizing CD8+ cells in vitro to said peptide and administering the sensitized cells to the subject in a sterile medium.

A vaccine is provided for preventing or treating human papilloma virus 16 (HPV 16) infection that induces a protective or therapeutic immune response, wherein said vaccine comprises a peptide of 20 amino acids or less comprising a cross-reactive peptide from the E6 protein of a related HPV strain, HPV 18, that has higher affinity for the HLA-A2.1 molecule than the corresponding epitope from HPV 16 itself, said peptide comprising the sequence X₁KLPDLCTEL(SEQ ID NO:1)X₂, wherein X₁ and X₂ are peptides of 0–11 amino acids in length comprising either native or non-native amino acid sequences and a pharmaceutically acceptable carrier. The vaccine can further comprise co-administering to the subject an immune adjuvant selected from non-specific immune adjuvants, subcellular microbial products and fractions, haptens, immunogenic proteins, immunomodulators, interferons, thymic hormones and colony stimulating factors. The peptide can be administered by administering to a subject an expression vector that expresses said peptide.

A method for monitoring or evaluating an immune response to human papilloma virus 16 (HPV 16) in a patient having the HLA-A2.1 type is provided, the method comprising incubating a T lymphocyte sample from the patient with a peptide of 20 amino acids or less comprising a cross-reactive peptide from the E6 protein of a related HPV strain, HPV 18, that has higher affinity for the HLA-A2.1 molecule than the corresponding epitope from HPV 16 itself, said peptide comprising the sequence X₁KLPDLCTEL(SEQ ID NO:1)X₂, wherein X₁ and X₂ are peptides of 0–11 amino acids in length comprising either native or non-native amino acid sequences and which peptide bears a binding motif corresponding to at least one HLA allele present in said patient, and detecting the presence of a T lymphocyte that recognizes the peptide.

A method screening for exposure to human papilloma virus 16 (HPV 16) in a patient having the HLA-A2.1 type is also provide, the method comprising incubating a T lymphocyte sample from the patient with a peptide of 20 amino acids or less comprising a cross-reactive peptide from the E6 protein of a related HPV strain, HPV 18, that has higher affinity for the HLA-A2.1 molecule than the corresponding epitope from HPV 16 itself, said peptide comprising the sequence X₁KLPDLCTEL(SEQ ID NO:1)X₂, wherein X₁ and X₂ are peptides of 0–11 amino acids in length comprising either native or non-native amino acid sequences and which peptide bears a binding motif corresponding to at least one HLA allele present in said patient, and detecting the presence of a T lymphocyte that recognizes the peptide, the presence of such a T lymphocyte indicating exposure to HPV.

A method is provided for inducing a cytotoxic T lymphocyte response and protective immunity against tumors induced by human papilloma virus 16 (HPV 16) using a cross-reactive peptide from the E6 protein of a related HPV strain, HPV 18, that has higher affinity for the HLA-A2.1 molecule than the corresponding epitope from PV 16 itself, said HPV18 peptide having the sequence X₁KLPDLCTEL (SEQ ID NO:1)X₂, wherein X₁ and X₂ are peptides of 0–11 amino acids.

As will be apparent from the discussion below, other methods and embodiments are also contemplated. Further, novel synthetic peptides produced by any of the methods described herein are also part of the invention.

DETAILED DESCRIPTION OF THE INVENTION

Figure 1:
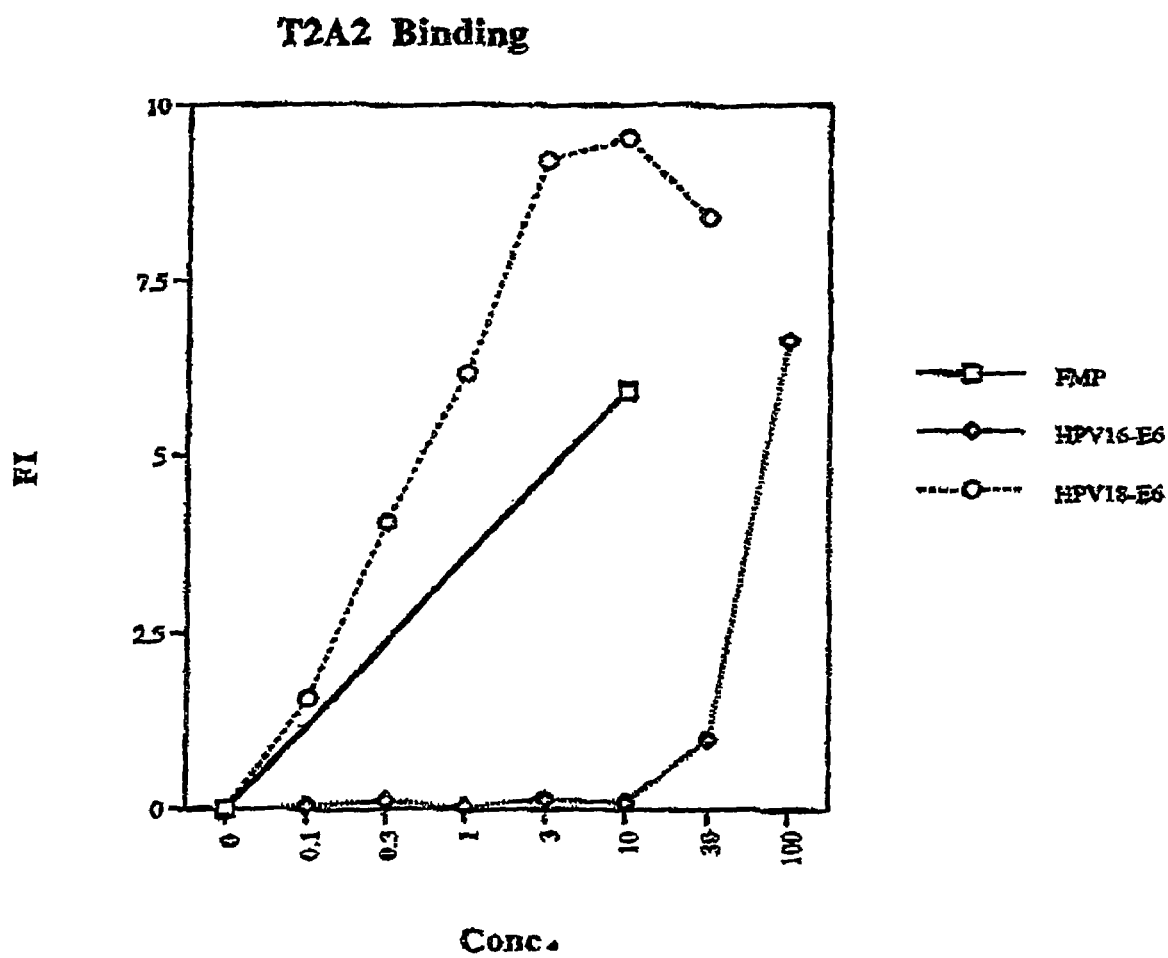
FIG. 1. HPV-18E6 (13–21) peptide binding to T2 cells show high affinity to HLA-A2 and is found to be higher than the homologous HPV-16E6 peptide.

The present invention provides an HPV-18E6 (13–21) peptide, KLPDLCTEL (SEQ ID NO:1), with a predicted HLA-A2 binding motif underlined, and shows that this peptide has a higher affinity for the HLA-A2.1 molecule than the corresponding epitope from HPV 16 itself.

The peptide epitopes in Table 1 and corresponding nucleic acid compositions of the present invention are useful for stimulating an immune response to HPV by stimulating the production of CTL or HTL responses. The peptide epitopes, which are derived directly or indirectly from native HPV amino acid sequences, are able to bind to HLA molecules and stimulate an immune response to HPV. The complete protein sequence from HPV-18E6 can be obtained from Genbank. Peptide epitopes and analogs thereof can also be readily determined from sequence information that may subsequently be discovered for heretofore unknown variants of HPV, as will be clear from the disclosure provided below.

The peptide epitopes of the invention have been identified. Also discussed below is that analog peptides have been derived and the binding activity for HLA molecules modulated by modifying specific amino acid residues to create peptide analogs exhibiting altered immunogenicity. Further, the present invention provides compositions and combinations of compositions that enable epitope-based vaccines that are capable of interacting with HLA molecules encoded by various genetic alleles to provide broader population coverage than prior vaccines.

Definitions

The invention can be better understood with reference to the following definitions, which are listed alphabetically:

An "antigen-presenting cell" is a specialized cell that express class II MHC proteins on its cell surface. Short peptides associate non-covalently with the surface class II MHC proteins which are then detected by other T cells such as T helper cells (HTL or helper T lymphocytes). Types of antigen presenting cells include, macrophages, B cells, and dendritic cells.

A "cytotoxic T cell" is a cell which will kill another cell that has foreign macromolecules on its surface. Frequently these foreign macromolecules will be peptides non-covalently bound to cell surface class I MHC molecules. Most, but not all cytotoxic T cells express surface CD8 protein. A small percentage of cytotoxic T cells express CD4 on their cell surface and a small percentage of cytotoxic T cells do not express either CD4 or CD8 on their cell surface. Cytotoxic T cell, CTL and Tc cell will be used interchangeably herein.

An "epitope" is a set of amino acid residues which is involved in recognition by a particular immunoglobulin, or in the context of T cells, those residues necessary for recognition by T cell receptor proteins and/or Major Histocompatibility Complex (MHC) receptors. In an immune system setting, in vivo or in vitro, an epitope is the collective features of a molecule, such as primary, secondary and tertiary peptide structure, and charge, that together form a site recognized by an immunoglobulin, T cell receptor or HLA molecule. Throughout this disclosure epitope and peptide are often used interchangeably.

It is to be appreciated that protein or peptide molecules that comprise an epitope of the invention as well as additional amino acid(s) are still within the bounds of the invention. In certain embodiments, there is a limitation on the length of a peptide of the invention which is not otherwise a construct. An embodiment that is length-limited occurs when the protein/peptide comprising an epitope of the invention comprises a region (i.e., a contiguous series of amino acids) having 100% identity with a native sequence. In order to avoid the definition of epitope from reading, e.g. on whole natural molecules, there is a limitation on the length of any region that has 100% identity with a native peptide sequence. Thus, for a peptide comprising an epitope of the invention and a region with 100% identity with a native peptide sequence (and is not otherwise a construct), the region with 100% identity to a native sequence generally has a length as indicated.

"Human Leukocyte Antigen" or "HLA" is a human class I or class II Major Histocompatibility Complex (MHC) protein (see, e.g., Stites, et al., IMMUNOLOGY, 8$^{TH}$ ED., Lange Publishing, Los Altos, Calif. (1994).

Peptide binding may be determined using assay systems including those using: live cells (e.g., Ceppellini et al., *Nature* 339:392, 1989; Christnick et al., *Nature* 352:67, 1991; Busch et al., *Int. Immunol.* 2:443, 1990; Hill et al., *J. Immunol.* 147:189, 1991; del Guercio et al., *J. Immunol.* 154:685, 1995), cell free systems using detergent lysates (e.g., Cerundolo et al., *J. Immunol.* 21:2069, 1991), immobilized purified MHC (e.g., Hill et al., *J. Immunol.* 152,2890, 1994; Marshall et al., *J. Immunol.* 152:4946, 1994), ELISA systems (e.g., Reay et al., *EMBO J.* 11:2829, 1992), surface plasmon resonance (e.g., Khilko et al., *J. Biol. Chem.* 268:15425, 1993); high flux soluble phase assays (Hammer et al., *J. Exp. Med.* 180:2353, 1994), and measurement of class I MHC stabilization or assembly (e.g., Ljunggren et al., *Nature* 346:476, 1990; Schumacher et al., *Cell* 62:563, 1990; Townsend et al, *Cell* 62:285, 1990; Parker et al., *J. Immunol.* 149:1896, 1992, which are incorporated herein by reference in their entireties, but also for their teaching regarding peptide binding assays).

The terms "identical" or percent "identity," in the context of two or more peptide sequences, refer to two or more sequences or subsequences that are the same or have a specified percentage of amino acid residues that are the same, when compared and aligned for maximum correspondence over a comparison window, as measured using a sequence comparison algorithm or by manual alignment and visual inspection.

An "immunogenic peptide" or "peptide epitope" is a peptide that comprises an allele-specific motif or supermotif such that the peptide will bind an HLA molecule and induce a CTL and/or HTL response. Thus, immunogenic peptides of the invention are capable of binding to an appropriate HLA molecule and thereafter inducing an HLA-restricted cytotoxic or helper T cell response to the antigen from which the immunogenic peptide is derived.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment An "isolated" epitope refers to an epitope that does not include the whole sequence of the antigen or polypeptide from which the epitope was derived. Typically the "isolated" epitope does not have attached thereto additional amino acids that result in a sequence that has 100% identity with a native sequence. The native sequence can be a sequence such as a tumor-associated antigen from which the epitope is derived.

A "lymphocyte" is a white blood cell derived from a stem cell of the primary lymphoid organs and which are responsible for mediating the immune response. The term lymphocyte includes T cells, B cells and Natural Killer cells "Major Histocompatibility Complex" or "MHC" is a cluster of genes that plays a role in control of the cellular interactions responsible for physiologic immune responses. In humans, the MHC complex is also known as the HLA complex. For a detailed description of the MHC and HLA complexes, see, Paul, FUNDAMENTAL IMMUNOLOGY, 3$^{RD}$ ED., Raven Press, New York, 1993.

The term "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs are typically different for each protein encoded by each human HLA allele and differ in the pattern of the primary and secondary anchor residues.

A "non-native" sequence or "construct" refers to a sequence that is not found in nature ("non-naturally occurring"). Such sequences include, e.g., peptides that are lipidated or otherwise modifed and polyepitopic compositions that contain epitopes that are non contiguous in a native protein sequence.

The term "peptide" is used interchangeably with "oligopeptide" in the present specification to designate a series of residues, typically L-amino acids, connected one to the other, typically by peptide bonds between the α-amino and carboxyl groups of adjacent amino acids. The preferred CTL-inducing peptides of the invention are 13 residues or less in length and usually consist of between about 8 and about 11 residues, preferably 9 or 10 residues. The preferred HTL-inducing oligopeptides are less than about 50 residues in length and usually consist of between about 6 and about 30 residues, more usually between about 12 and 25, and often between about 15 and 20 residues.

"pharmaceutically acceptable" refers to a generally non-toxic, inert, and/or physiologically compatible composition.

A "pharmaceutical excipient" comprises a material such as an adjuvant, a carrier, pH-adjusting and buffering agents, tonicity adjusting agents, wetting agents, preservative, and the like.

A "protective immune response" or "therapeutic immune response" refers to a CTL and/or an HTL response to an antigen derived from an infectious agent or a tumor antigen, which prevents or at least partially arrests disease symptoms or progression. The immune response may also include an antibody response which has been facilitated by the stimulation of helper T cells.

The term "residue" refers to an amino acid or amino acid mimetic incorporated into an oligopeptide by an amide bond or amide bond mimetic.

"Synthetic peptide" refers to a peptide that is man-made using such methods as chemical synthesis or recombinant DNA technology.

As used herein, a "vaccine" is a composition that contains one or more peptides of the invention. There are numerous embodiments of vaccines in accordance with the invention, such as by a cocktail of one or more peptides; one or more epitopes of the invention comprised by a polyepitopic peptide; or nucleic acids that encode such peptides or polypeptides, e.g., a minigene that encodes a monoepitopic or polyepitopic peptide. The peptides or polypeptides can optionally be modified, such as by lipidation, addition of targeting or other sequences. HLA class I-binding peptides of the invention can be admixed with, or linked to, HLA class II-binding peptides, to facilitate activation of both cytotoxic T lymphocytes and helper T lymphocytes. Vaccines can also comprise peptide-pulsed antigen presenting cells, e.g., dendritic cells.

The nomenclature used to describe peptide compounds follows the conventional practice wherein the amino group is presented to the left (the N-terminus) and the carboxyl group to the right (the C-terminus) of each amino acid residue. When amino acid residue positions are referred to in a peptide epitope they are numbered in an amino to carboxyl direction with position one being the position closest to the amino terminal end of the epitope, or the peptide or protein of which it may be a part In the formulae representing selected specific embodiments of the present invention, the amino- and carboxyl-terminal groups, although not specifically shown, are in the form they would assume at physiologic pH values, unless otherwise specified. In the amino acid structure formulae, each residue is generally represented by standard three letter or single letter designations.

The L-form of an amino acid residue is represented by a capital single letter or a capital first letter of a three-letter symbol, and the D-form for those amino acids having D-forms is represented by a lower case single letter or a lower case three letter symbol. Glycine has no asymmetric carbon atom and is simply referred to as "Gly" or G. Symbols for the amino acids are shown below.

| Single Letter Symbol | Three Letter Symbol | Amino Acids |
| --- | --- | --- |
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Stimulation of CTL and HTL Responses

The mechanism by which T cells recognize antigens has been delineated during the past ten years. Based on our understanding of the immune system we have developed efficacious peptide epitope vaccine compositions that can induce a therapeutic or prophylactic immune response to HPV in a broad population. For an understanding of the value and efficacy of the claimed compositions, a brief review of immunology-related technology is provided.

A complex of an HLA molecule and a peptidic antigen acts as the ligand recognized by HLA-restricted T cells (Buus, S. et al., *Cell* 47:1071, 1986; Babbitt, B. P. et al., *Nature* 317:359, 1985; Townsend, A. and Bodmer, H., *Annu. Rev. Immunol.* 7:601, 1989; Germain, R. N., *Annu. Rev. Immunol.* 11:403, 1993). Through the study of single amino acid substituted antigen analogs and the sequencing of endogenously bound, naturally processed peptides, critical residues that correspond to motifs required for specific binding to HLA antigen molecules have been identified (see, e.g., Southwood, et al, *J. Immunol.* 160:3363, 1998; Rammensee, et al., *Immunogenetics* 41:178, 1995; Rammensee et al, SYFPEITHI, access via web at: http://134.2.96.221/scripts.hlaserver.d11/home.htm; Sette, A. and Sidney, J. *Curr. Opin. Immunol.* 10:478, 1998; Engelhard, V. H., *Curr. Opin. Immunol.* 6:13, 1994; Sette, A. and Grey, H. M., *Curr. Opin. Immunol* 4:79, 1992; Sinigaglia, F. and Hammer, J. *Curr. Biol.* 6:52, 1994; Ruppert et al., *Cell* 74:929–937, 1993; Kondo et al., *J. Immunol.* 155:4307–4312, 1995; Sidney et al., *J. Immunol.* 157:3480–3490, 1996; Sidney et al., *Human Immunol* 45:79–93, 1996, which are incorporated herein by reference in their entireties, but also for their teaching regarding peptide binding motifs).

Furthermore, x-ray crystallographic analysis of HLA-peptide complexes has revealed pockets within the peptide binding cleft of HLA molecules which accommodate, in an allele-specific mode, residues borne by peptide ligands; these residues in turn determine the HLA binding capacity of the peptides in which they are present. (See, e.g., Madden, D. R. *Annu. Rev. Immunol.* 13:587, 1995; Smith, et al., *Immunity* 4:203, 1996; Fremont et al., *Immunity* 8:305, 1998; Stem et al., *Structure* 2:245, 1994; Jones, E. Y. *Curr. Opin. Immunol.* 9:75, 1997; Brown, J. H. et al., *Nature* 364:33, 1993; Guo, H. C. et al., *Proc. Natl. Acad. Sci. USA* 90:8053, 1993; Guo, H. C. et al., *Nature* 360:364, 1992; Silver, M. L. et al., *Nature* 360:367, 1992; Matsumura, M. et al., *Science* 257:927, 1992; Madden et al., *Cell* 70:1035, 1992; Fremont, D. H. et al., *Science* 257:919, 1992; Saper, M. A., Bjorkman, P. J. and Wiley, D. C., *J. Mol. Biol.* 219:277, 1991, which are incorporated herein by reference in their entireties, but also for their teaching regarding peptide binding.)

Accordingly, the definition of class I and class II allele-specific HLA binding motifs, or class I or class II supermotifs allows identification of regions within a protein that have the potential of binding particular HLA antigen(s).

Peptide Epitope Binding Motifs and Supermotifs

In the past few years evidence has accumulated to demonstrate that a large fraction of HLA class I and class II molecules can be classified into a relatively few supertpes, each characterized by largely overlapping peptide binding repertoires, and consensus structures of the main peptide binding pockets.

For HLA molecule pocket analyses, the residues comprising the B and F pockets of HLA class I molecules as described in crystallographic studies were analyzed (see, e.g., Guo, H. C. et al., *Nature* 360:364, 1992; Saper, M. A., Bjorkman, P. J. and Wiley, D. C., *J. Mol. Biol.* 219:277, 1991; Madden, D. R., Garboczi, D. N. and Wiley, D. C., *Cell* 75:693, 1993; Parham, P., Adams, E. J., and Arnett, K. L., *Immunol. Rev.* 143:141, 1995). In these analyses, residues 9, 45, 63, 66, 67, 70, and 99 were considered to make up the B pocket; and the B pocket was deemed to determine the specificity for the amino acid residue in the second position of peptide ligands. Similarly, residues 77, 80, 81, and 116 were considered to determine the specificity of the P pocket; the F pocket was deemed to determine the specificity for the C-terminal residue of a peptide ligand bound by the HLA class I molecule.

Through the study of single amino acid substituted antigen analogs and the sequencing of endogenously bound, naturally processed peptides, critical residues required for allele-specific binding to HLA molecules have been identified. The presence of these residues correlates with binding affinity for HLA molecules. The identification of motifs and/or supermotifs that correlate with high and intermediate affinity binding is an important issue with respect to the identification of immunogenic peptide epitopes for the inclusion in a vaccine. Kast et al. (*J. Immunol.* 152:3904–3912, 1994) have shown that motif-bearing peptides account for 90% of the epitopes that bind to allele-specific HLA class I molecules. In this study all possible peptides of 9 amino acids in length and overlapping by eight amino acids (240 peptides), which cover the entire sequence of the E6 and E7 proteins of human papillomavirus type 16, were evaluated for binding to five allele-specific HLA molecules that are expressed at high frequency among different ethnic groups. This unbiased set of peptides allowed an evaluation of the predictive value of HLA class I motifs. From the set of 240 peptides, 22 peptides were identified that bound to an allele-specific HLA molecule with high or intermediate affinity. Of these 22 peptides, 20 (i.e. 91%) were motif-bearing. Thus, this study demonstrates the value of motifs for the identification of peptide epitopes for inclusion in a vaccine: application of motif-based identification techniques eliminates screening of 90% of the potential epitopes in a target antigen protein sequence.

Peptides of the present invention as set forth in Table 1 may also comprise epitopes that bind to MHC class II molecules. A greater degree of heterogeneity in both size and binding frame position of the motif, relative to the N and C termini of the peptide, exists for class II peptide ligands. This increased heterogeneity of HLA class II peptide ligands is due to the structure of the binding groove of the HLA class II molecule which, unlike its class I counterpart, is open at both ends. Crystallographic analysis of HLA class II DRB*0101-peptide complexes showed that the major energy of binding is contributed by peptide residues complexed with complementary pockets on the DRB*0101 molecules. An important anchor residue engages the deepest hydrophobic pocket (see, e.g., Madden, D. R. *Ann. Rev. Immunol.* 13:587, 1995) and is referred to as position 1 (P1). P1 may represent the N-terminal residue of a class II binding peptide epitope, but more typically is flanked towards the N-terminus by one or more residues. Other studies have also pointed to an important role for the peptide residue in the $6^{th}$ position towards the C-terminus, relative to P1, for binding to various DR molecules.

Thus, peptides of the present invention as set forth in Table 1 are identified by any one of several HLA-specific amino acid motifs. If the presence of the motif corresponds to the ability to bind several allele-specific HLA antigens, it is referred to as a supermotif. The HLA molecules that bind to peptides that possess a particular amino acid supermotif are collectively referred to as an HLA "supertype."

Immune Response-Stimulating Peptide Analogs

In general, CTL and HTL responses are not directed against all possible epitopes. Rather, they are restricted to a few "immunodominant" determinants (Zinkernagel, et al, *Adv. Immunol.* 27:5159, 1979; Bennink, et al, *J. Exp. Med.* 168:19351939, 1988; Rawle, et al., *J. Immunol.* 146:3977–3984, 1991). It has been recognized that immunodominance (Benacerraf, et al, *Science* 175:273–279, 1972) could be explained by either the ability of a given epitope to selectively bind a particular HLA protein (determinant selection theory) (Vitiello, et al., *J. Immunol.* 131: 1635, 1983); Rosenthal, et al., *Nature* 267:156–158, 1977), or to be selectively recognized by the existing TCR (T cell receptor) specificities (repertoire theory) (Klein, J., IMMUNOLOGY, THE SCIENCE OF SELFNONSELF DISCRIMINATION, John Wiley & Sons, New York pp. 270–310, 1982). It has been demonstrated that additional factors, mostly linked to processing events, can also play a key role in dictating, beyond strict immunogenicity, which of the many potential determinants will be presented as immunodominant (Sercarz, et al., *Annu. Rev. Immunol.* 11:729–766, 1993).

The concept of dominance and subdominance is relevant to immunotherapy of both infectious diseases and cancer. For example, in the course of chronic viral disease, recruitment of subdominant epitopes can be important for successful clearance of the infection, especially if dominant CTL or HTL specificities have been inactivated by functional tolerance, suppression, mutation of viruses and other mechanisms (Franco, et al., *Curr. Opin. Immunol.* 7:524–531, 1995; Zajac, et al., *J. Exp. Med.* 188:2205–2213, 1998). In the case of cancer and tumor antigens, CTLs recognizing at least some of the highest binding affinity peptides might be functionally inactivated. Lower binding affinity peptides are preferentially recognized at these times, and may therefore be preferred in therapeutic or prophylactic anti-cancer vaccines.

In particular, it has been noted that a significant number of epitopes derived from known non-viral tumor associated antigens (TAA) bind HLA class I with intermediate affinity ($IC_{50}$ in the 50–500 nM range). For example, it has been found that 8 of 15 known TAA peptides recognized by tumor infiltrating lymphocytes (TIL) or CTL bound in the 50–500 nM range. (These data are in contrast with estimates that 90% of known viral antigens were bound by HLA class I molecules with $IC_{50}$ of 50 nM or less, while only approximately 10% bound in the 50–500 nM range (Sette, et al., *J. Immunol.*, 153:558–5592, 1994). In the cancer setting this phenomenon is probably due to elimination or functional inhibition of the CTL recognizing several of the highest binding peptides, presumably because of T cell tolerization events.

Without intending to be bound by theory, it is believed that because T cells to dominant epitopes may have been clonally deleted, selecting subdominant epitopes may allow existing T cells to be recruited, which will then lead to a therapeutic or prophylactic response. However, the binding of HLA molecules to subdominant epitopes is often less vigorous than to dominant ones. Accordingly, there is a need to be able to modulate the binding affinity of particular immunogenic epitopes for one or more HLA molecules, and thereby to modulate the immune response elicited by the peptide, for example to prepare analog peptides which elicit a more vigorous response. This ability would greatly enhance the usefulness of peptide-based vaccines and therapeutic agents.

To ensure that an analog peptide, when used as a vaccine, actually elicits a CTL response to the native epitope in vivo (or, in the case of class II epitopes, elicits helper T cells that cross-react with the wild type peptides), the analog peptide may be used to immunize T cells in vitro from individuals of the appropriate HLA allele. Thereafter, the immunized cells' capacity to induce lysis of wild type peptide sensitized target cells is evaluated. It will be desirable to use as antigen presenting cells, cells that have been either infected, or transfected with the appropriate genes, or, in the case of class II epitopes only, cells that have been pulsed with whole protein antigens, to establish whether endogenously produced antigen is also recognized by the relevant T cells.

Another embodiment for generating effective peptide analogs involves the substitution of residues that have an adverse impact on peptide stability or solubility in, e.g., a liquid environment. This substitution may occur at any position of the peptide epitope. For example, a cysteine (C) can be substituted out in favor of α-amino butyric acid. Due to its chemical nature, cysteine has the propensity to form disulfide bridges and sufficiently alter the peptide structurally so as to reduce binding capacity. Substituting α-amino butyric acid for C not only alleviates this problem, but actually improves binding and crossbinding capability in certain instances (see, e.g. the review by Sette et al., In: *Persistent Viral Infections*, Eds. R. Ahmed and I. Chen, John Wiley & Sons, England, 1999). Substitution of cysteine with α-amino butyric acid may occur at any residue of a peptide epitope, i.e. at either anchor or non-anchor positions.

Preparation of Peptide Epitopes

Peptides in accordance with the invention can be prepared synthetically, by recombinant DNA technology or chemical synthesis, or from natural sources such as native tumors or pathogenic organisms. Peptide epitopes may be synthesized individually (monoepitopes) or as polyepitopic peptides. Although the peptide will preferably be substantially free of other naturally occurring host cell proteins and fragments thereof, in some embodiments the peptides may be synthetically conjugated to native fragments or particles.

The peptides in accordance with the invention and as set forth in Example 1 can be a variety of lengths, and either in their neutral (uncharged) forms or in forms which are salts. The peptides in accordance with the invention are either free of modifications such as glycosylation, side chain oxidation, or phosphorylation; or they contain these modifications, subject to the condition that modifications do not destroy the biological activity of the peptides as described herein.

The peptides of the invention can be prepared in a wide variety of ways. For the preferred relatively short size, the peptides can be synthesized in solution or on a solid support in accordance with conventional techniques. Various automatic synthesizers are commercially available and can be used in accordance with known protocols. (See, for example, Stewart & Young, SOLID PHASE PEPTIDE SYNTHESIS, 2D. ED., Pierce Chemical Co., 1984, which is incorporated herein by reference in its entirety, but also for its teaching regarding peptide synthesis methods). Further, individual peptide epitopes can be joined using chemical ligation to produce larger peptides that are still within the bounds of the invention.

Alternatively, recombinant DNA technology can be employed wherein a nucleotide sequence which encodes an immunogenic peptide of interest is inserted into an expression vector, transformed or transfected into an appropriate host cell and cultivated under conditions suitable for expression. These procedures are generally known in the art, as described generally in Sambrook et al., MOLECULAR CLONING, A LABORATORY MANUAL, Cold Spring Harbor Press, Cold Spring Harbor, N.Y. (1989), which is incorporated herein by reference in its entirety, but also for its teaching regarding recombinant expression of peptides. Thus, recombinant polypeptides which comprise one or more peptide sequences of the invention can be used to present the appropriate T cell epitope.

The nucleotide coding sequence for peptide epitopes of the preferred lengths contemplated herein can be synthesized by chemical techniques, for example, the phosphotriester method of Matteucci, et al., *J. Am. Chem. Soc.* 103: 3185 (1981)), which is incorporated herein by reference in its entirety, but also for its teaching regarding recombinant nucleic acids for expression of peptides. Peptide analogs can be made simply by substituting the appropriate and desired nucleic acid base(s) for those that encode the native peptide sequence; exemplary nucleic acid substitutions are those that encode an amino acid defined by the motifs herein. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host For example, promoter sequences compatible with bacterial hosts are provided in plasmids containing convenient restriction sites for insertion of the desired coding sequence. The resulting expression vectors are transformed into suitable bacterial hosts. Of course, yeast, insect or mammalian cell hosts may also be used, employing suitable vectors and control sequences.

It is often preferable that the peptide epitope be as small as possible while still maintaining substantially all of the immunologic activity of the native protein. When possible, it may be desirable to optimize HLA class I binding peptide epitopes of the invention to a length of about 8 to about 13 amino acid residues, preferably 9 to 10. HLA class II binding peptide epitopes may be optimized to a length of about 6 to about 11 amino acids in length. Preferably, the peptide epitopes are commensurate in size with endogenously processed pathogen-derived peptides or tumor cell peptides that are bound to the relevant HLA molecules, however, the identification and preparation of peptides of other lengths can also be carried out using the techniques described herein.

In alternative embodiments, peptides of the invention can be linked as a polyepitopic peptide, or as a minigene that encodes a monoepitopic or polyepitopic peptide.

Assays to Detect T-Cell Responses

The HLA binding peptides identified in Example 1 can be tested for the ability to elicit a T-cell response. The preparation and evaluation of motif-bearing peptides are described in PCT publications WO 94/20127 and WO 94/03205), which are incorporated herein by reference in their entirety, but also for their teaching regarding motif-bearing peptides. Briefly, peptides comprising epitopes from a particular antigen are synthesized and tested for their ability to bind to the appropriate HLA proteins. These assays may involve evaluating the binding of a peptide of the invention to purified HLA class I molecules in relation to the binding of a radioiodinated reference peptide. Alternatively, cells expressing empty class I molecules (i.e. lacking peptide therein) may be evaluated for peptide binding by immunofluorescent staining and flow microfluorimetry. Other assays that may be used to evaluate peptide binding include peptide-dependent class I assembly assays and/or the inhibition of CTL recognition by peptide competition. Those peptides that bind to the class I molecule, typically with an affinity of 500 nM or less, are further evaluated for their ability to serve as targets for CTLs derived from infected or immunized individuals, as well as for their capacity to induce primary in vitro or in vivo CTL responses that can give rise to CTL populations capable of reacting with selected target cells associated with a disease. Corresponding assays are used for evaluation of HLA class II binding peptides. HLA class II motif-bearing peptides that are shown to bind, typically at an affinity of 1000 nM or less, are further evaluated for the ability to stimulate HTL responses.

Conventional assays utilized to detect T cell responses include proliferation assays, lymphokine secretion assays, direct cytotoxicity assays, and limiting dilution assays. For example, antigen-presenting cells that have been incubated with a peptide can be assayed for the ability to induce CTL responses in responder cell populations. Antigen-presenting cells can be normal cells such as peripheral blood mononuclear cells or dendritic cells. Alternatively, mutant non-human mammalian cell lines that are deficient in their ability to load class I molecules with internally processed peptides and that have been transfected with the appropriate human class I gene, may be used to test for the capacity of the peptide to induce in vitro primary CTL responses.

Peripheral blood mononuclear cells (PBMCs) may be used as the responder cell source of CTL precursors. The appropriate antigen-presenting cells are incubated with peptide, after which the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the antigen from which the peptide sequence was derived.

More recently, a method has been devised which allows direct quantification of antigen-specific T cells by staining with Fluorescein-labelled HLA tetrameric complexes (Altman, J. D. et al., *Proc. Natl. Acad. Sci. USA* 90:10330,1993; Altman, J. D. et al., *Science* 274:94, 1996), which are incorporated herein by reference in their entirety, but also for their teaching regarding quantification of T cells). Other relatively recent technical developments include staining for intracellular lymphokines, and interferon release assays or ELISPOT assays. Tetramer staining, intracellular lympholine staining and ELISPOT assays all appear to be at least 10-fold more sensitive than more conventional assays (Lalvani, A. et al., *J. Exp. Med.* 186:859, 1997; Dunbar, P. R. et al., *Curr. Biol.* 8:413, 1998; Murali-Krishna, K. et al., *Immunity* 8:177, 1998, which are incorporated herein by reference in their entirety, but also for their teaching regarding quantification of T cells).

HTL activation may also be assessed using such techniques known to those in the art such as T cell proliferation and secretion of lymphokines, e.g. IL-2 (see, e.g. Alexander et al., *Immunity* 1:751–761, 1994).

Alternatively, immunization of HLA transgenic mice can be used to determine immunogenicity of peptide epitopes. Several transgenic mouse models including mice with human A2.1, A11 (which can additionally be used to analyze HLA-A3 epitopes), and B7 alleles have been characterized and others (e.g., transgenic mice for HLA-A1 and A24) are being developed. HLA-DR1 and HLA-DR3 mouse models have also been developed. Additional transgenic mouse models with other HLA alleles may be generated as necessary. Mice may be immunized with peptides emulsified in Incomplete Freund's Adjuvant and the resulting T cells tested for their capacity to recognize peptide-pulsed target cells and target cells transfected with appropriate genes. CTL responses may be analyzed using cytotoxicity assays described above. Similarly, HTL responses may be analyzed using such assays as T cell proliferation or secretion of lymphokines.

Use of Peptide Epitopes as Diagnostic Agents and for Evaluating Immune Responses In one embodiment of the invention, HLA class I and class II binding peptides as described in Example 1 can be used as reagents to evaluate an immune response. The immune response to be evaluated can be induced by using as an immunogen any agent that may result in the production of antigen-specific CTLs or HTLs that recognize and bind to the peptide epitope(s) to be employed as the reagent. The peptide reagent need not be used as the immunogen. Assay systems that can be used for such an analysis include relatively recent technical developments such as tetramers, staining for intracellular lymphokines and interferon release assays, or ELISPOT assays.

For example, a peptide of the invention may be used in a tetramer staining assay to assess peripheral blood mononuclear cells for the presence of antigen-specific CTLs following exposure to a tumor cell antigen or an immunogen. The HLA-tetrameric complex is used to directly visualize antigen-specific CTLs (see, e.g., Ogg et al, *Science* 279:2103–2106, 1998; and Altman et al., *Science* 174:94–96, 1996, which are incorporated herein by reference in their entirety, but also for their teaching regarding quantification of T cells) and determine the frequency of the antigen-specific CTL population in a sample of peripheral blood mononuclear cells. A tetramer reagent using a peptide of the invention may be generated as follows: A peptide that binds to an HLA molecule is refolded in the presence of the corresponding HLA heavy chain and $\beta_2$-microglobulin to generate a trimolecular complex. The complex is biotinylated at the carboxyl terminal end of the heavy chain at a site that was previously engineered into the protein. Tetramer formation is then induced by the addition of streptavidin. By means of fluorescently labeled streptavidin, the tetramer can be used to stain antigen-specific cells. The cells may then be identified, for example, by flow cytometry. Such an analysis may be used for diagnostic or prognostic purposes. Cells identified by the procedure can also be used for therapeutic purposes.

Peptides of the invention may also be used as reagents to evaluate immune recall responses. (see, e.g., Bertoni et al., *J. Clin. Invest.* 100:503–513, 1997 and Penna et al., *J. Exp. Med.* 174:1565–1570, 1991, which are incorporated herein by reference in their entirety, but also for their teaching regarding quantification of T cells.) For example, patient PBMC samples from individuals with HPV infection may be analyzed for the presence of antigen-specific CTLs or HTLs using specific peptides. A blood sample containing mononuclear cells may be evaluated by cultivating the PBMCs and stimulating the cells with a peptide of the invention. After an appropriate cultivation period, the expanded cell population may be analyzed, for example, for cytotoxic activity (CTL) or for HTL activity.

The peptides may also be used as reagents to evaluate the efficacy of a vaccine. PBMCs obtained from a patient vaccinated with an immunogen may be analyzed using, for example, either of the methods described above. The patient is HLA typed, and peptide epitope reagents that recognize the allele-specific molecules present in that patient are selected for the analysis. The immunogenicity of the vaccine is indicated by the presence of epitope-specific CTLs and/or HTLs in the PBMC sample.

The peptides of the invention may also be used to make antibodies, using techniques well known in the art (see, e.g. *Current Protocols in Immunology*, Wiley/Greene, N.Y.; and *Antibodies A Laboratory Manual*, Harlow and Lane, Cold Spring Harbor Laboratory Press, 1989, which is incorporated herein by reference in its entirety, but also for its teaching regarding antibody preparation), which may be useful as reagents to diagnose or monitor cancer. Such antibodies include those that recognize a peptide in the context of an HLA molecule, i.e., antibodies that bind to a peptide-MHC complex.

Vaccine Compositions

Vaccines and methods of preparing vaccines that contain an immunogenically effective amount of one or more peptides as described herein are further embodiments of the invention. Once appropriately immunogenic epitopes have been defined, they can be sorted and delivered by various means, herein referred to as "vaccine" compositions. Such vaccine compositions can include, for example, lipopeptides (e.g., Vitiello, A. et al., *J. Clin. Invest.* 95:341, 1995), peptide compositions encapsulated in poly(DL-lactideco-glycolide) ("PLG") microspheres (see, e.g., Eldridge, et al., *Molec. Immunol.* 28:287–294, 1991: Alonso et al., *Vaccine* 12:299–306, 1994; Jones et al., *Vaccine* 13:675–681, 1995), peptide compositions contained in immune stimulating complexes (ISCOMS) (see, e.g. Takahashi et al., *Nature* 344: 873–875, 1990; Hu et al., *Clin Exp Immunol.* 113:235–243, 1998), multiple antigen peptide systems (MAPs) (see e.g., Tam, J. P., *Proc. Natl. Acad. Sci. U.S.A.* 85:5409–5413, 1988; Tam, J. P., *J. Immunol. Methods* 196:17–32, 1996), viral delivery vectors (Perkus, M. E. et al., In: *Concepts in vaccine development*, Kaufmann, S. H. E., ed., p. 379, 1996; Chakrabarti, S. et al., *Nature* 320:535, 1986; Hu, S. L. et al., *Nature* 320:537, 1986; Kieny, M.-P. et al., *AIDS Bio/Technology* 4:790, 1986; Top, F. H. et al, *J. Infect. Dis.* 124:148, 1971; Chanda, P. K. et al., *Virology* 175:535, 1990), particles of viral or synthetic origin (e.g., Kofler, N. et al., *J. Immunol. Methods.* 192:25, 1996; Eldridge, J. H. et al., *Sem. Hematol* 30:16, 1993; Falo, L. D., Jr. et al., *Nature Med.* 7:649, 1995), adjuvants (Warren, H. S., Vogel, F. R., and Chedid, L. A. *Annu. Rev. Immunol.* 4:369, 1986; Gupta, R. K. et al., *Vaccine* 11:293, 1993), liposomes (Reddy, R. et al., *J. Immunol.* 148:1585, 1992; Rock, K. L., *Immunol. Today* 17:131, 1996), or, naked or particle absorbed cDNA (Ulmer, J. B. et al., *Science* 259:1745, 1993; Robinson, H. L., Hunt, L. A., and Webster, R. G., *Vaccine* 11:957, 1993; Shiver, J. W. et al., In: *Concepts in vaccine development*, Kaufmann, S. H. E., ed., p. 423, 1996; Cease, K. B., and Berzofsky, J. A., *Annu. Rev. Immunol.* 12:923, 1994 and Eldridge, J. H. et al., *Sem. Hematol.* 30:16, 1993, which are incorporated herein by reference in their entirety, but also for their teaching regarding vaccine compositions). Toxin-targeted delivery technologies, also known as receptor mediated targeting, such as those of Avant Immunotherapeutics, Inc. (Needham, Mass.) may also be used.

Vaccines of the invention include nucleic acid-mediated modalities. DNA or RNA encoding one or more of the peptides of the invention can also be administered to a patient. This approach is described, for instance, in Wolff et. al., *Science* 247:1465 (1990) as well as U.S. Pat. Nos. 5,580,859; 5,589,466; 5,804,566; 5,739,118; 5,736,524; 5,679,647; WO 98/04720 (which are incorporated herein by reference in their entirety, but also for their teaching regarding vaccine compositions); and in more detail below. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687, which is incorporated herein by reference in its entirety, but also for its teaching regarding DNA vaccines).

For therapeutic or prophylactic immunization purposes, the peptides of the invention can also be expressed by viral or bacterial vectors. Examples of expression vectors include attenuated viral hosts, such as vaccinia or fowlpox. As an example of this approach, vaccinia virus is used as a vector to express nucleotide sequences that encode the peptides of the invention. Upon introduction into a host bearing a tumor, the recombinant vaccinia virus expresses the immunogenic peptide, and thereby elicits a host CTL and/or HTL response. Vaccinia vectors and methods useful in immunization protocols are described in, e.g., U.S. Pat. No. 4,722,848. Another vector is BCG (Bacille Calmette Guerin). BCG vectors are described in Stover et al., *Nature* 351:456–460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Furthermore, vaccines in accordance with the invention encompass compositions of one or more of the claimed peptide(s) as described in Example 1. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glycerylcysteinlyseryl-serine ($P_3CSS$).

Upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs and/or HTLs specific for the desired antigen. Consequently, the host becomes at least partially immune to later infection, or at least partially resistant to developing an ongoing chronic infection, or derives at least some therapeutic benefit when the antigen was tumor-associated.

In some embodiments it may be desirable to combine the class I peptide components with components that induce or facilitate neutralizing antibody responses to the target antigen of interest, particularly to viral envelope antigens. A preferred embodiment of such a composition comprises class I and class II epitopes in accordance with the invention.

A vaccine of the invention can also include antigen-presenting cells, such as dendritic cells, as a vehicle to present peptides of the invention. Vaccine compositions can be created in vitro, following dendritic cell mobilization and harvesting, whereby loading of dendritic cells occurs in vitro. For example, dendritic cells are transfected, e.g., with a minigene in accordance with the invention. The dendritic cell can then be administered to a patient to elicit immune responses in vivo.

Antigenic peptides are used to elicit a CTL and/or HTL response ex vivo, as well. The resulting CTL or HTL cells, can be used to treat tumors in patients that do not respond to other conventional forms of therapy, or will not respond to a therapeutic vaccine peptide or nucleic acid in accordance with the invention. Ex vivo CTL or HTL responses to a particular tumor-associated antigen are induced by incubating in tissue culture the patients, or genetically compatible, CTL or HTL precursor cells together with a source of antigen-presenting cells (APC), such as dendritic cells, and the appropriate immunogenic peptide. After an appropriate incubation time (typically about 7–28 days), in which the precursor cells are activated and expanded into effector cells, the cells are infused back into the patient, where they will destroy (CTL) or facilitate destruction (HTL) of their specific target cell (an infected cell or a tumor cell). Transfected dendritic cells may also be used as antigen presenting cells.

The vaccine compositions of the invention can also be used in combination with antiviral drugs such as interferon-α, or other treatments for viral infection.

Exemplary epitopes that may be utilized in a vaccine to treat or prevent HPV infection are set out in Example 1 and Table 1.

If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polyepitopic peptide, the size minimization objective is balanced against the need to integrate any spacer sequences between epitopes in the polyepitopic protein. Spacer amino acid residues can be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

Specific embodiments of the polyepitopic compositions of the present invention include a pharmaceutical composition comprising a pharmaceutically acceptable carrier and combination of motif-bearing peptides that are immunologically cross-reactive with peptides of HPV, wherein at least one of the peptides bears a motif of SEQ ID NO. 1, and a second peptide selected from Table 1.

Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes is described below and in, e.g. An, L. and Whitton, J. L., *J. Virol.* 71:2292, 1997; Thomson, S. A. et al., *J. Immunol.* 157:822, 1996; Whitton, J. L. et al., *J. Virol.* 67:348, 1993; Hanke, R. et al., *Vaccine* 16:426, 1998, which are incorporated herein by reference in their entirety, but also for their teaching regarding multi-epitope minigene vaccine compositions. For example, a multi-epitope DNA plasmid encoding SEQ ID NO. 1 and an endoplasmic reticulum-translocating signal sequence can be engineered.

The immunogenicity of a multi-epitopic minigene can be tested in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a CTL response and 2.) that the induced CTLs recognized cells expressing the encoded epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA class I epitopes, HLA class II epitopes, a ubiquitination signal sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30–100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses. Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids can also be used in the formulation (see, e.g., as described by WO 93/24640; Mannino & Gould-Fogerite, *BioTechniques* 6(7): 682 (1988); U.S. Pat. No. 5,279,833; WO 91/06309; and Felgner, et al., *Proc. Nat'l Acad. Sci. USA* 84:7413 (1987), which are incorporated herein by reference in their entirety, but also for their teaching regarding DNA vaccine compositions. In addition, glycolipids, fusogenic liposomes, peptides and compounds referred to collectively as protective, interactive, non-condensing compounds (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates both production of, and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (IP) for lipid-complexed DNA). Twenty-one days after immunization, splenocytes are harvested and restimulated for 1 week in the presence of peptides encoding each epitope being tested. Thereafter, for CTL effector cells, assays are conducted for cytolysis of peptide-loaded, $^{51}$Cr-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is evaluated in transgenic mice in an analogous manner.

Alternatively, the nucleic acids can be administered using ballistic delivery as described, for instance, in U.S. Pat. No. 5,204,253, which is incorporated herein by reference in its entirety, but also for its teaching regarding ballistic DNA delivery. Using this technique, particles comprised solely of DNA are administered. In a further alternative embodiment, DNA can be adhered to particles, such as gold particles.

Combinations of CTL Peptides with Helper Peptides

Vaccine compositions comprising the peptides of the present invention, or analogs thereof, which have immuno-stimulatory activity may be modified to provide desired attributes, such as improved serum half life, or to enhance immunogenicity.

For instance, the ability of the peptide KLPDLCTEL (SEQ ID NO:1) to induce CTL activity can be enhanced by linking the peptide to a sequence which contains at least one epitope that is capable of inducing a T helper cell response such as DRAHYNI (SEQ ID NO. 2).

Particularly preferred CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues. Alternatively, the CTL peptide may be linked to the T helper peptide without a spacer. The amino terminus of either the immunogenic peptide or the T helper peptide may be acylated.

The HTL peptide epitope can also be modified to alter its biological properties. For example, peptides comprising HTL epitopes can contain D-amino acids to increase their resistance to proteases and thus extend their serum half-life. Also, the epitope peptides of the invention can be conjugated to other molecules such as lipids, proteins or sugars, or any other synthetic compounds, to increase their biological activity. Specifically, the T helper peptide can be conjugated to one or more palmitic acid chains at either the amino or carboxyl termini.

In some embodiments it may be desirable to include in the pharmaceutical compositions of the invention at least one component which primes cytotoxic T lymphocytes. Lipids have been identified as agents capable of priming CTL in vivo against viral antigens. For example, palmitic acid residues can be attached to the ε-and α-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant In a preferred embodiment, a particularly effective immunogenic comprises palmitic acid attached to ε- and α-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinly-seryl-serine ($P_3CSS$) can be used to prime virus specific CTL when covalently attached to an appropriate peptide. (See, e.g., Deres, et al., *Nature* 342:561, 1989). Peptides of the invention can be coupled to $P_3CSS$, for example, and the lipopeptide administered to an individual to specifically prime a CTL response to the target antigen. Moreover, because the induction of neutralizing antibodies can also be primed with $P_3CSS$-conjugated epitopes, two such compositions can be combined to more effectively elicit both humoral and cell-mediated responses to infection.

As noted herein, additional amino acids can be added to the termini of a peptide to provide for ease of linking peptides one to another, for coupling to a carrier support or larger peptide, for modifying the physical or chemical properties of the peptide or oligopeptide, or the like. Amino acids such as tyrosine, cysteine, lysine, glutamic or aspartic acid, or the like, can be introduced at the C- or N-terminus of the peptide or oligopeptide, particularly class I peptides. However, it is to be noted that modification at the carboxyl terminus of a CTL epitope may, in some cases, alter binding characteristics of the peptide. In addition, the peptide or oligopeptide sequences can differ from the natural sequence by being modified by terminal-$NH_2$ acylation, e.g., by alkanoyl ($C_1$—$C_{20}$) or thioglycolyl acetylation, terminal-carboxyl amidation, e.g., ammonia, methylamine, etc. In some instances these modifications may provide sites for linking to a support or other molecule.

Vaccine Compositions Comprising Dendritic Cells (DC) Pulsed with CTL and/or HTL Peptides An embodiment of a vaccine composition in accordance with the invention comprises ex vivo administration of peptides to PBMC, or isolated DC therefrom, from the patient's blood. A pharmaceutical to facilitate harvesting of DC can be used, such as GM-CSF/IL4. After pulsing the DC with peptides and prior to reinfusion into patients, the DC are washed to remove unbound peptides. In this embodiment, a vaccine comprises peptide-pulsed DCs which present the pulsed peptide epitopes complexed with HLA molecules on their surfaces. The vaccine is then administered to the patient.

Administration of Vaccines for Therapeutic or Prophylactic Purposes

The peptides of the present invention and pharmaceutical and vaccine compositions of the invention are useful for administration to mammals, particularly humans, to treat and/or prevent HPV infection. Vaccine compositions containing the peptides of the invention are administered to a patient infected with HPV or to an individual susceptible to, or otherwise at risk for, HPV infection to elicit an immune response against HPV antigens and thus enhance the patient's own immune response capabilities. In therapeutic applications, peptide and/or nucleic acid compositions are administered to a patient in an amount sufficient to elicit an effective CTL and/or HTL response to the virus antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

The vaccine compositions of the invention may also be used purely as prophylactic agents. Generally the dosage for an initial prophylactic immunization generally occurs in a unit dosage range where the lower value is about 1, 5, 50, 500, or 1000 µg of peptide and the higher value is about 10,000; 20,000; 30,000; or 50,000 µg. Dosage values for a human typically range from about 500 µg to about 50,000 µg per 70 kilogram patient. This is followed by boosting dosages of between about 1.0 µg to about 50,000 µg of peptide administered at defined intervals from about four weeks to six months after the initial administration of vaccine. The immunogenicity of the vaccine may be assessed by measuring the specific activity of CTL and HTL obtained from a sample of the patient's blood.

As noted above, peptides comprising CTL and/or HTL epitopes of the invention induce immune responses when presented by HLA molecules and contacted with a CTL or HTL specific for an epitope comprised by the peptide. The manner in which the peptide is contacted with the CTL or HTL is not critical to the invention. For instance, the peptide can be contacted with the CTL or HTL either in vivo or in vitro. If the contacting occurs in vivo, the peptide itself can be administered to the patient, or other vehicles, e.g., DNA vectors encoding one or more peptides, viral vectors encoding the peptide(s), liposomes and the like, can be used, as described herein. When the peptide is contacted in vitro, the vaccinating agent can comprise a population of cells, e.g., peptide-pulsed dendritic cells, or TAA-specific CTLs, which have been induced by pulsing antigen-presenting cells in vitro with the peptide. Such a cell population is subsequently administered to a patient in a therapeutically effective dose.

The peptides or DNA encoding them can be administered individually or as fusions of one or more peptide sequences.

For pharmaceutical compositions, the immunogenic peptides of the invention, or DNA encoding them, are generally administered to an individual already infected with HPV. The peptides or DNA encoding them can be administered individually or as fusions of one or more peptide sequences. Those in the incubation phase or the acute phase of infection can be treated with the immunogenic peptides separately or in conjunction with other treatments, as appropriate.

For therapeutic use, administration should generally begin at the first diagnosis of HPV infection. This is followed by boosting doses until at least symptoms are substantially abated and for a period thereafter. In chronic infection, loading doses followed by boosting doses may be required.

The peptide or other compositions used for the treatment or prophylaxis of HPV infection can be used, e.g., in persons who have not manifested symptoms of disease but who act as a disease vector. In this context, it is generally important to provide an amount of the peptide epitope delivered by a mode of administration sufficient to effectively stimulate a cytotoxic T cell response; compositions which stimulate helper T cell responses can also be given in accordance with this embodiment of the invention.

The dosage for an initial therapeutic immunization generally occurs in a unit dosage range where the lower value is about 1, 5, 50, 500, or 1000 µg of peptide and the higher value is about 10,000; 20,000; 30,000; or 50,000 µg. Dosage values for a human typically range from about 500 µg to about 50,000 µg per 70 kilogram patient. Boosting dosages of between about 1.0 µg to about 50000 µg of peptide pursuant to a boosting regimen over weeks to months may be administered depending upon the patient's response and condition as determined by measuring the specific activity of CTL and HTL obtained from the patient's blood. The peptides and compositions of the present invention may be employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

The pharmaceutical compositions for therapeutic treatment are intended for parenteral, topical, oral, intrathecal or local administration. Preferably, the pharmaceutical compositions are administered parentally, e.g. intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier. A variety of aqueous carriers may be used, e.g. water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of the peptide composition is typically included in a pharmaceutical composition that comprises a human unit dose of an acceptable carrier, preferably an aqueous carrier, and is administered in a volume of fluid that is known by those of skill in the art to be used for administration of such compositions to humans (see, e.g., *Remington's Pharmaceutical Sciences*, 17$^{th}$ Edition, A. Gennaro, Editor, Mack Publishing Co., Easton, Pa., 1985).

The peptides of the invention may also be administered via liposomes, which serve to target the peptides to a particular tissue, such as lymphoid tissue, or to target selectively to infected cells, as well as to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g. Szoka, et al., *Ann. Rev. Biophys. Bioeng.* 9:467 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, and more preferably at a concentration of 25%–75%.

For aerosol administration, the immunogenic peptides are preferably supplied in finely divided form along with a surfactant and propellant Typical percentages of peptides are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included, as desired, as with, e.g., lecithin for intranasal delivery.

EXAMPLES

Example 1

Immunogenic Peptide Isolated from HPV-18E6 Protein

The peptide KLPDLCTEL(SEQ ID NO:1) identified in the HPV-18E6 protein (amino acids 13–21) contains a predicted HLA-A2 binding motif. To determine if this peptide could bind to this class I MHC molecule, the peptide was synthesized, fluorescently labeled and tested for binding to T2A2 cells. T2A2 cells are T cells which possess the HLA-A2 molecule on their cell surface. Also tested in this binding assay were the flu matrix peptide (FMP) which is known to bind to the HLA-A2 molecule with high affinity and the peptide KLPQLCTEL (SEQ ID NO. 10), from the HPV-16E6 protein (amino acids 13–21). The results are shown in FIG. 1. All three peptides bound to the HLA-A2 molecules on the surface of the T2A2 cells. Surprisingly, the peptide of the invention, KLPDLCTEL(SEQ ID NO:1), bound to the HLA-A2 molecule with a higher affinity than did either the FMP peptide or the homologous peptide from the HPV-16E6 protein. The only difference between the HPV-18E6 and HPV-16E6 peptides is at amino acid position 4. The HPV-18E6 peptide contains a D residue at amino acid 4 while the HPV-16E6 peptide contains a Q residue at this position. Because the KLPDLCTEL(SEQ ID NO:1) peptide isolated from HPV-18E6 bound to the HLA-A2 molecule with approximately 100 fold higher affinity than did the homologous KLPQLCTEL (SEQ ID NO. 10) peptide isolated from HPV-16E6, the KLPDLCTEL(SEQ ID NO:1) peptide should be more efficient at generating an immune response to HPV than the homologous HPV-16E6 peptide.

Figure 2:
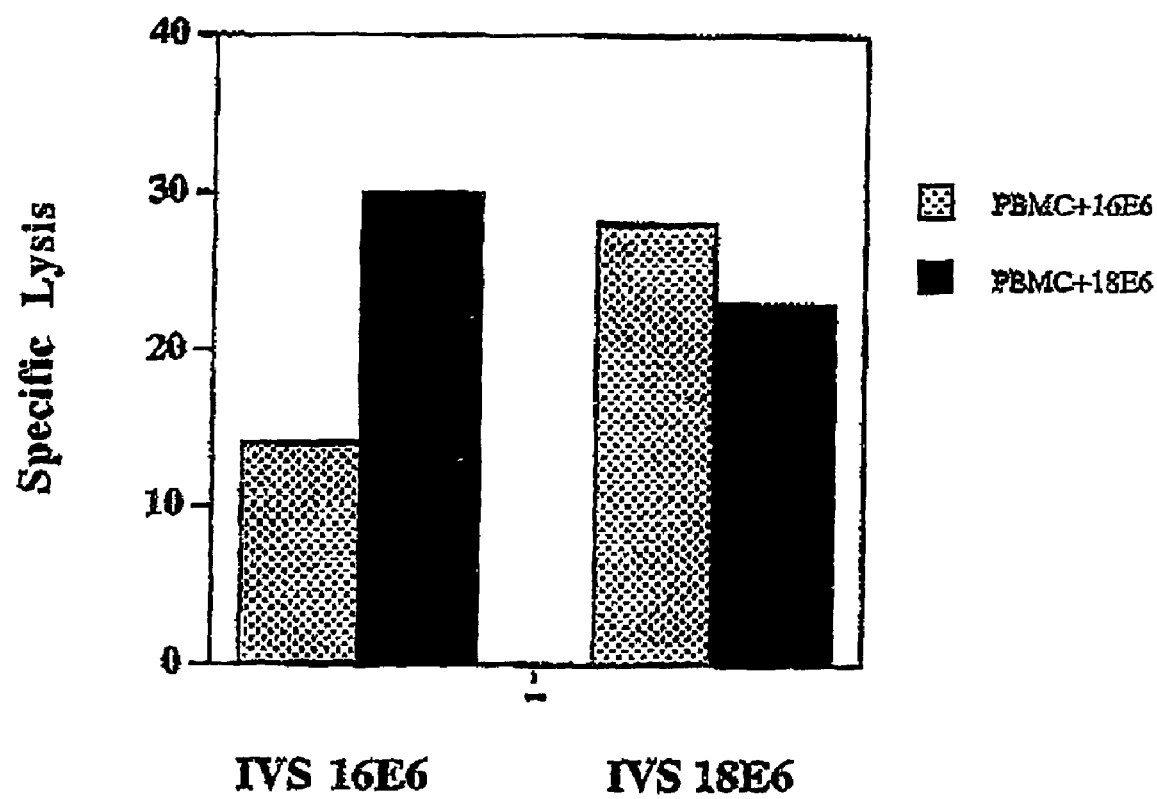
FIG. 2. Lymphocytes obtained from HLA-A2 patients were stimulated in vitro with HPV-18E6 peptides were found to specifically lyse autologous PBMC pulsed with either HPV-16E6 or HPV-18E6 peptides. Similarly T cells stimulated with HPV-16E6 peptides were found to lyse autologous PBMC pulsed with either HPV-16 E6 or HPV-18E6 peptides.

To determine if lymphocytes stimulated in vitro with either the HPV-18E6 peptide (SEQ ID NO. 1) or the HPV-16E6 peptide (SEQ ID NO. 10) would recognize and lyse peripheral blood mononuclear cells (PBMCs) pulsed with these peptides, the following experiment was performed. Lymphocytes isolated from a patient known to carry and express the HLA-A2 allele were stimulated in vitro (IVS) with either the HPV-18E6 peptide (SEQ ID NO. 1) or the HPV-16E6 peptide (SEQ ID NO. 10) at a 10 μm concentration for 1–3 weeks. Autologous PBMC target cells were radiolabeled with $^{51}$Cr and pulsed with either the HPV-18E6 peptide (SEQ ID NO. 1) or the HPV-16E6 peptide (SEQ ID NO. 10). Each of the IVS lymphocyte populations were then mixed with each of the pulsed and labeled PBMC target cells and specific lysis was measured. The results are shown in FIG. 2. Lymphocytes IVS with either the HPV-18E6 peptide (SEQ ID NO. 1) or the HPV-16E6 peptide (SEQ ID NO. 10) were able to lyse PBMCs which were pulsed with either the HPV-18E6 peptide (SEQ ID NO. 1) or the HPV-16E6 peptide (SEQ ID NO. 10) and had either the HPV-18E6 peptide (SEQ ID NO. 1) or the HPV-16E6 (SEQ ID NO. 10) peptide on their cell surface. These data indicate that the HPV-18E6 peptide (SEQ ID NO. 1) would be useful for evaluating T cell responses in patients infected with HPV, or individuals who have been vaccinated with either the HPV-18E6 peptide (SEQ ID NO. 1) or the HPV-16E6 peptide (SEQ ID NO. 10).

These data indicate that the HPV-18E6 peptide (SEQ ID NO. 1) is able to bind to HLA-A2 molecule on the cell surface and is able to elicit an immune response. This peptide, either alone, or in combination with other peptides (see Table 1) would be useful in vaccine compositions and methods of using the peptides of Table 1.

TABLE 1

Immunogenic peptides.

| Peptide | Class type | SEQ ID NO. |
|---|---|---|
| KLPDLCTEL (SEQ ID NO:1) | Class I | SEQ ID NO.1 |
| DRAHYNI | Class II | SEQ ID NO.2 |
| IVCPICSQ | Class I | SEQ ID NO.4 |
| LLMGTLGIV | Class I | SEQ ID NO.5 |
| TLGIVCPIC | Class I | SEQ ID NO.6 |
| LLMGTLGIVCP | Class I | SEQ ID NO.7 |
| TLGIVCPI | Class I | SEQ ID NO.8 |
| GTLGIVCPI | Class I | SEQ ID NO.9 |

Additional immunogenic peptides have been identified which contain motifs which bind to either class I or class II MHC molecules (see e.g., Kast, et al., *J. Immunol.* 152: 3904–3912 (1994), U.S. Pat. No. 6,183,746, and U.S. Pat. No. 6,004,557) and are found in Table I. These peptides can be combined with the immunogenic peptide KLPDLCTEL (SEQ ID NO:1) isolated from HPV-18E6 protein to create polyepitopic peptides which would bind to multiple HLA class I molecules or to both HLA class I (CTL) and class II (HTL) molecules. The peptides can be directly linked to the peptide KLPDLCTEL(SEQ ID NO:1) or be connected via a spacer peptide. Spacers are typically selected from e.g., Ala, Gly or other neutral spacers of non-polar amino acids or neutral polar amino acids. It is understood that the optionally present spacer need not be comprised of the same residues and thus may be a hetero- or homo-oligomer. When present the spacer will usually be at least one to two residues, and more usually three to six residues. The class I (CTL) peptide epitope can be linked to the class II (HTL) peptide epitope either directly or via a spacer at the amino or carboxy terminus of the class I peptide.

As discussed above, the immunogenic peptides of Table I can be combined to create a polyepitopic peptide of 20 amino acids or less and of the structure $X_1$KLPDLCTEL (SEQ ID NO:1)$X_2$ where $X_1$ and $X_2$ are peptides of 0–11 amino acid residues in length and can include a spacer sequence.

Example 2

Peptide Composition for Prophylactic Uses

Vaccine compositions of the present invention are used to prevent HPV infection in persons who are at risk for such infection. For example, a monoepitopic peptide or a polyepitopic peptide epitope composition (or a nucleic acid comprising the same) containing a single HPV-18E6 epitope or multiple CTL and/or HTL epitopes such as those in Table 1, is administered to individuals at risk for HPV infection. The composition is provided as a single lipidated polypeptide that encompasses the single or multiple epitopes. The vaccine is administered in an aqueous carrier comprised of Freunds Incomplete Adjuvant The dose of peptide for the initial immunization is from about 1 to about 50,000 µg, generally 100–5,000 µg, for a 70 kg patient. The initial administration of vaccine is followed by booster dosages at 4 weeks followed by evaluation of the magnitude of the immune response in the patient, by techniques that determine the presence of epitope-specific CTL populations in a PBMC sample. Additional booster doses are administered as required. The composition is found to be both safe and efficacious as a prophylaxis against HPV infection.

Alternatively, the monoepitopic peptide or the polyepitopic peptide compositions can be administered as a nucleic acid in accordance with methodologies known in the art and disclosed herein.

Example 3

Construction of Minizene Multi-Epitope DNA Plasmids

This example provides guidance for the construction of a minigene expression plasmid. Minigene plasmids may, of course, contain various configurations of CTL and/or HTL epitopes or epitope analogs as described herein.

A minigene expression plasmid may include multiple CTL and/or HTL peptide epitopes. Preferred epitopes are identified, for example, in Table 1. The selected CTL and HTL epitopes are then incorporated into a minigene for expression in an expression vector.

This example illustrates the methods to be used for construction of such a minigene-bearing expression plasmid. Other expression vectors that may be used for minigene compositions are available and known to those of skill in the art.

The minigene DNA plasmid contains a consensus Kozak sequence and a consensus murine kappa Ig-light chain signal sequence followed by CTL and/or HTL epitopes selected in accordance with principles disclosed herein.

Overlapping oligonucleotides encoding the selected peptides are synthesized and HPLC-purified. The oligonucleotides encode the selected peptide epitopes as well as appropriate linker nucleotides, Kozak sequence, signal sequence, and stop codon. The final multiepitope minigene is assembled by extending the overlapping oligonucleotides in reactions using PCR. A Perkin/Elmer 9600 PCR machine is used and a total of 30 cycles are performed using the following conditions: 95° C. for 15 sec, annealing temperature (5° below the lowest calculated Tm of each primer pair) for 30 sec, and 72° C. for 1 min.

For the PCR reaction, 5 µg of each of the two oligonucleotides are annealed and extended: Oligonucleotides are combined in 100 µl reactions containing Pfu polymerase buffer (1x=10 mM KCL, 10 mM $(NH_4)_2SO_4$, 20 mM Tris-chloride, pH 8.75, 2 mM $MgSO_4$, 0.1% Triton X-100, 100 µg/ml BSA), 0.25 mM each dNTP, and 2.5 U of Pfu polymerase. The full-length dimer product is gel-purified and cloned into pCR-blunt (Invitrogen) and individual clones are screened by sequencing.

Example 4

The Plasmid Construct and the Degree to Which it Induces Immunogenicity

The degree to which the plasmid construct prepared using the methodology outlined in Example 3 is able to induce immunogenicity is evaluated through in vivo injections into mice and subsequent in vitro assessment of CTL and HTL activity, which are analyzed using cytotoxicity and proliferation assays, respectively, as detailed e.g., Alexander et al., *Immunity* 1:751–761, 1994. For example, to assess the capacity of a pMin minigene construct that contains the HLA-A2 motif epitope KLPDLCTEL(SEQ ID NO:1) to induce CTLs in vivo, HLA-A2.1/$K^b$ transgenic mice are immunized intramuscularly with 100 µg of naked cDNA. As a means of comparing the level of CTLs induced by cDNA immunization, a control group of animals is also immunized with an actual peptide composition that comprises the epitope synthesized as a single polypeptide as they would be encoded by the minigene.

Splenocytes from immunized animals are stimulated twice with each of the respective compositions (peptide epitopes encoded in the minigene or the peptide), then assayed for peptide-specific cytotoxic activity in a $^{51}Cr$ release assay. The results indicate the magnitude of the CTL response directed against the A2-restricted epitope, thus indicating the in vivo immunogenicity of the minigene vaccine and polypeptide vaccine. It is, therefore, found that the minigene elicits immune responses directed toward the HLA-A2 peptide epitope as does the peptide vaccine.

To assess the capacity of a class II epitope encoding minigene to induce HTLs in vivo, I-$A^b$ restricted mice, for example, are immunized intramuscularly with 100 µg of plasmid DNA. As a means of comparing the level of HTLs induced by DNA immunization, a group of control animals is also immunized with an actual peptide composition emulsified in complete Freund's adjuvant.

CD4+ T cells, i.e. HTLs, are purified from splenocytes of immunized animals and stimulated with each of the respective compositions (peptides encoded in the minigene). The HTL response is measured using a $^3H$-thymidine incorporation proliferation assay, (see, e.g., Alexander et al. *Immunity* 1:751–761, 1994) the results indicate the magnitude of the HTL response, thus demonstrating the in vivo immunogenicity of the minigene.

Alternatively, plasmid constructs can be evaluated in vitro by testing for epitope presentation by APC following transduction or transfection of the APC with an epitope-expressing nucleic acid construct. Such a study determines "antigenicity" and allows the use of human APC. The assay determines the ability of the epitope to be presented by the APC in a context that is recognized by a T cell by quantifying the density of epitope-HLA class I complexes on the cell surface. Quantitation can be performed by directly measuring the amount of peptide eluted from the APC (see, e.g., Sijts et al., *J. Immunol.* 156:683–692, 1996; Demotz et al., *Nature* 342:682–684, 1989); or the number of peptide-HLA class I complexes can be estimated by measuring the amount of lysis or lymphokine release induced by infected or transfected target cells, and then determining the concentration of peptide necessary to obtained equivalent levels of lysis or lymphokine release (see, e.g., Kageyama et al., *J. Immunol.* 154:567–576, 1995).

Example 5

Use of Peptides to Evaluate an Immune Response

In-vitro T Cell Cytotoxic Assay:

T cell cytotoxicity is measured by the standard $^{51}$Cr-release assay. Briefly, target cells are radiolabeled with $Na_2$ $^{51}CrO_4$. The patient's PBMC (which have been previously stimulated with an HPV peptide of Example 1 at 10 μm concentration for 1 to 3 weeks) are added to the labeled target cells in the presence or absence of the peptide. Cell lysis is determined by the specific release of $^{51}$Cr (specific lysis). Target cells are autologous B-LCL or T2 cells pulsed with the peptide. If there is a detectable pre-immunization specific lysis, a 2.0 fold increase in the lytic units will be considered a positive response. If there is no detectable pre-immunization specific lysis, a post-immunization specific lysis of less than 10% above the controls will be considered a positive response.

Assessment of IFN-Gamma Response:

To assess the IFN-gamma response, $3 \times 10^6$ PBMC per well are cultured in a 24-well plate±HPV peptide of Example 1/or tetanus toxoid +20 IU/ml IL-2 for 6–19 days period. For positive control wells, PBMC are cultured in wells containing FMP with IL-2 and without HPV peptide of Example 1. Culture supernatants are harvested and stored frozen at (−20° C.) until assayed for IFN-gamma by ELISA. Titrated amounts of culture supernatants are tested using commercially available ELISA kits (Endogen, GIBCO, or Genzyme). The amount of IFN-gamma in culture supernatants is determined by comparing experimental results to standard curves generated with known amounts of recombinant human IFN-gamma. Stimulator cells will be both autologous PBMC pulsed with peptides and autologous tumor, if available. A positive response will be taken as a 2-fold increase over background as long as at least 50 pg/ml are made. The intra-assay variability is less than 5%.

In-Vitro T Cell Proliferation Assay:

An autologous patient's PBMC is incubated in-vitro with tetanus toxoid (Tt) and evaluated for Tt-induced proliferation following up to 5 days of incubation. Cultures are pulsed with $^3$H-thymidine for the final 18–24 hours of their culture. Proliferation is measured and quantitated by the incorporation of $^3$H-thymidine. A proliferation of more than three fold above control will be considered as a positive response.

Example 6

Use of Peptide Epitopes to Evaluate Recall Responses

The peptide epitopes of Example 1 are used as reagents to evaluate T cell responses, such as acute or recall responses, in patients. Such an analysis may be performed on patients who have recovered from infection, who have been vaccinated with an HPV vaccine of the invention, or who have been vaccinated containing peptide epitopes homologous to the peptides in Table 1.

PBMC from vaccinated individuals or individuals who have recovered from an infection are separated on Ficoll-Histopaque density gradients (Sigma Chemical Co., St. Louis, Mo.), washed three times in HBSS (GIBCO Laboratories), resuspended in RPMI-1640 (GIBCO Laboratories) supplemented with L-glutamine (2 mM), penicillin (50 U/ml), streptomycin (50 μg/ml), and Hepes (10 mM) containing 10% heat-inactivated human AB serum (complete RPMI) and plated using microculture formats. A synthetic peptide comprising an epitope of the invention is added at 10 μg/ml to each well and DRAHYNI (SEQ ID NO. 2) is added at 1 μg/ml to each well as a source of T cell help during the first week of stimulation.

In the microculture format, $4 \times 10^5$ PBMC are stimulated with peptide in 8 replicate cultures in 96-well round bottom plate in 100 μl/well of complete RPMI. On days 3 and 10, 100 ml of complete RPMI and 20 U/ml final concentration of rIL-2 are added to each well. On day 7 the cultures are transferred into a 96-well flat-bottom plate and restimulated with peptide, rIL-2 and $10^5$ irradiated (3,000 rad) autologous feeder cells. The cultures are tested for cytotoxic activity on day 14. A positive CTL response requires two or more of the eight replicate cultures to display greater than 10% specific $^{51}$Cr release, based on comparison with uninfected control subjects as previously described (Rehermann, et al., *Nature Med.* 2:1104,1108, 1996; Rehermann et al., *J. Clin. Invest.* 97:1655–1665, 1996; and Rehermann et al *J. Clin. Invest.* 98:1432–1440, 1996).

Target cell lines are autologous and allogeneic EBV-transformed B-LCL that are either purchased from the American Society for Histocompatibility and Immunogenetics (ASHI, Boston, Mass.) or established from a pool of patients as described (Guilhot, et al. *J. Virol* 66:2670–2678, 1992) or T2 cells.

Cytotoxicity assays are performed in the following manner. Target cells consist of either allogeneic HLA-matched or autologous EBV-transformed B lymphoblastoid cell line that are incubated overnight with the synthetic peptide epitope of the invention at 10 μM, and labeled with 100 μCi of $^{51}$Cr (Amersham Corp., Arlington Heights, Ill.) for 1 hour after which they are washed four times with HBSS.

Cytolytic activity is determined in a standard 4-h, split well $^{51}$Cr release assay using U-bottomed 96 well plates containing 3,000 targets/well. Stimulated PBMC are tested at effector/target (E/T) ratios of 20–50:1 on day 14. Percent cytotoxicity is determined from the formula: 100×[(experimental release-spontaneous release)/maximum release-spontaneous release)]. Maximum release is determined by lysis of targets by detergent (2% Triton X-100; Sigma Chemical Co., St. Louis, Mo.). Spontaneous release is <25% of maximum release for all experiments.

The results of such an analysis indicate the extent to which HLA-restricted CTL populations have been stimulated by previous exposure to HPV or an HPV vaccine.

The class II restricted HTL responses may also be analyzed. Purified PBMC are cultured in a 96-well flat bottom plate at a density of $1.5 \times 10^5$ cells/well and are stimulated with 10 µg/ml synthetic peptide containing the DRAHYNI (SEQ ID NO.2) peptide, or PHA. Cells are routinely plated in replicates of 4–6 wells for each condition. After seven days of culture, the medium is removed and replaced with fresh medium containing 10 U/ml IL-2. Two days later, 1 µCi $^3$H-thymidine is added to each well and incubation is continued for an additional 18 hours. Cellular DNA is then harvested on glass fiber mats and analyzed for $^3$H-thymidine incorporation. Antigen-specific T cell proliferation is calculated as the ratio of $^3$H-thymidine incorporation in the presence of antigen divided by the $^3$H-thymidine incorporation in the absence of antigen.

Example 7

Induction Of Specific CTL Response In Humans

A human clinical trial for an immunogenic composition comprising CTL and HTL epitopes of Example 1, including SEQ ID NO:1, is set up as an IND Phase I, dose escalation study and carried out as a randomized, double-blind, placebo-controlled trial. Such a trial is designed, for example, as follows:

A total of about 27 subjects are enrolled and divided into 3 groups:

Group I: 3 subjects are injected with placebo and 6 subjects are injected with 5 µg of peptide composition;

Group II: 3 subjects are injected with placebo and 6 subjects are injected with 50 µg peptide composition;

Group m: 3 subjects are injected with placebo and 6 subjects are injected with 500 µg of peptide composition.

After 4 weeks following the first injection, all subjects receive a booster inoculation at the same dosage.

The endpoints measured in this study relate to the safety and tolerability of the peptide composition as well as its immunogenicity. Cellular immune responses to the peptide composition are an index of the intrinsic activity of this the peptide composition, and can therefore be viewed as a measure of biological efficacy. The following summarize the clinical and laboratory data that relate to safety and efficacy endpoints.

Safety: The incidence of adverse events is monitored in the placebo and drug treatment group and assessed in terms of degree and reversibility.

Evaluation of Vaccine Efficacy: For evaluation of vaccine efficacy, subjects are bled before and after injection. Peripheral blood mononuclear cells are isolated from fresh heparinized blood by Ficoll-Hypaque density gradient centrifugation, aliquoted in freezing media and stored frozen. Samples are assayed for CTL and HTL activity.

The vaccine is found to be both safe and efficacious.

Example 8

Administration of Vaccine Compositions Using Dendritic Cells

Vaccines comprising peptide epitopes of Example 1, including SEQ ID NO:1, may be administered using dendritic cells. In this example, the peptide-pulsed dendritic cells can be administered to a patient to stimulate a CTL response in vivo. In this method dendritic cells are isolated, expanded, and pulsed with a vaccine comprising peptide CTL and HTL epitopes of the invention. The dendritic cells are infused back into the patient to elicit CTL and HTL responses in vivo. The induced CTL and HTL then destroy (CTL) or facilitate destruction (HTL) of the specific target HPV-infected cells that bear the proteins from which the epitopes in the vaccine are derived.

Alternatively, Ex vivo CTL or HTL responses to a particular tumor-associated antigen can be induced by incubating in tissue culture the patient's, or genetically compatible, CTL or HTL precursor cells together with a source of antigen-presenting cells, such as dendritic cells, and the appropriate immunogenic peptides. After an appropriate incubation time (typically about 7–28 days), in which the precursor cells are activated and expanded into effector cells, the cells are infused back into the patient, where they will destroy (CTL) or facilitate destruction (HTL) of their specific target cells, i.e., tumor cells.

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference.

What is claimed is:

1. A method for inducing an immune response against human papilloma virus 16 (HPV 16) comprising administering to a subject a composition, which is selected from a group consisting of:
   (i) a peptide of 20 amino acids or less comprising a cross-reactive peptide from the E6 protein of a related HPV strain, HPV 18, that has higher affinity for the HLA-A2.1 molecule than the corresponding epitope from HPV 16 itself, said peptide consisting of the sequence $X_1$KLPDLCTEL(SEQ ID NO:1)$X_2$, wherein $X_1$ and $X_2$ are peptides of 0–11 amino acids in length comprising contiguous HPV 18 E6 amino acid sequences;
   (ii) an antigen presenting cell pulsed with said peptide; and
   (iii) a cell sensitized in vitro to said peptide.

2. The method of claim 1, wherein the composition is in a pharmaceutically acceptable carrier.

3. The method of claim 1, wherein the composition is in a sterile medium.

4. The method of claim 2, further comprising co-administering to the subject an immune adjuvant selected from non-specific immune adjuvants, subcellular microbial products and fractions, haptens, immunogenic proteins, immunomodulators, interferons, thymic hormones and colony stimulating factors.

5. The method of claim 1, wherein the administration comprises sensitizing CD8+ cells in vitro to said peptide and administering the sensitized cells to the subject in a sterile medium.

6. A method for inducing an immune response against human papilloma virus 16 (HPV 16) comprising administering to a subject diagnosed with HPV16 infection a composition, which is selected from a group consisting of:
   (i) a peptide of 20 amino acids or less comprising a cross-reactive peptide from the E6 protein of a related HPV strain, HPV 18, that has higher affinity for the HLA-A2.1 molecule than the corresponding epitope from HPV 16 itself, said peptide consisting of the sequence $X_1$KLPDLCTEL(SEQ ID NO:1)$X_2$, wherein $X_1$ and $X_2$ are peptides of 0–11 amino acids in length comprising contiguous HPV 18 E6 amino acid sequences;
   (ii) an antigen presenting cell pulsed with said peptide; and
   (iii) a cell sensitized in vitro to said peptide.

* * * * *